(12) United States Patent
Chen et al.

(10) Patent No.: US 8,772,487 B2
(45) Date of Patent: Jul. 8, 2014

(54) FLUOROGENIC HYDRAZINE-SUBSTITUTED COMPOUNDS

(75) Inventors: Aimei Chen, Eugene, OR (US); Kyle Gee, Springfield, OR (US); Hee Chol Kang, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 291 days.

(21) Appl. No.: 12/864,038

(22) PCT Filed: Jan. 23, 2009

(86) PCT No.: PCT/US2009/031830
§ 371 (c)(1),
(2), (4) Date: Jul. 22, 2010

(87) PCT Pub. No.: WO2009/094536
PCT Pub. Date: Jul. 30, 2009

(65) Prior Publication Data
US 2010/0291547 A1    Nov. 18, 2010

Related U.S. Application Data

(60) Provisional application No. 61/023,191, filed on Jan. 24, 2008.

(51) Int. Cl.
*C07D 471/06* (2006.01)
*C07F 9/655* (2006.01)

(52) U.S. Cl.
CPC .......... *C07D 471/06* (2013.01); *C07F 9/65522* (2013.01)
USPC .............................. 546/47; 549/220; 549/394

(58) Field of Classification Search
None
See application file for complete search history.

(56) References Cited

U.S. PATENT DOCUMENTS

| | | |
|---|---|---|
| 4,386,150 A * | 5/1983 | Herchen et al. ............... 430/222 |
| 4,420,627 A | 12/1983 | Widiger |
| 4,711,955 A | 12/1987 | Ward et al. |
| 5,047,519 A | 9/1991 | Hobbs et al. |
| 5,049,673 A | 9/1991 | Tsien et al. |
| 5,352,803 A | 10/1994 | Mattingly |
| 5,362,628 A | 11/1994 | Haugland et al. |
| 5,405,975 A | 4/1995 | Kuhn et al. |
| 5,433,896 A | 7/1995 | Kang et al. |
| 5,453,517 A | 9/1995 | Kuhn et al. |
| 5,573,904 A | 11/1996 | Mattingly |
| 5,648,270 A | 7/1997 | Kuhn et al. |
| 5,714,327 A | 2/1998 | Houthoff et al. |
| 6,075,134 A | 6/2000 | Bertozzi et al. |
| 6,967,251 B2 | 11/2005 | Haugland et al. |
| 2005/0170363 A1 | 8/2005 | Reddington et al. |

FOREIGN PATENT DOCUMENTS

| | | |
|---|---|---|
| WO | WO-00/64988 | 11/2000 |
| WO | WO-2009/094536 | 7/2009 |

OTHER PUBLICATIONS

Byrn et al. Solid-State Chemistry of Drugs, 2nd ed. Chapter 11, "Hydrates and Solvates," p. 233-247.*
"Analyte." Definition from Biology-Online.org. Accessed Mar. 24, 2012. <http://www.biology-online.org/dictionary/Analyte>.*
Byrn et al. Solid-State Chemistry of Drugs, 2nd ed. (1999) Chapter 11, "Hydrates and Solvates," p. 233-247.*
PCT/US2009/031830; International Search Report and Written Opinion mailed Mar. 19, 2009.
PCT/US2009/031830; International Preliminary Report on Patentability mailed Aug. 5, 2010.
Otteneder, et al., "Reaction of Malondialdehyde-DNA adducts with Hydrazines-Development of a Facile Assay for Quantification of Malondialdehyde Equivalents in DNA", *Chem. Res. Toxicol.* vol. 15, 2002 ; pp. 312-318.

* cited by examiner

*Primary Examiner* — Alicia L Otton

(74) *Attorney, Agent, or Firm* — Life Technologies Corporation

(57) ABSTRACT

The present disclosure is directed to fluorogenic schiff base-forming dyes capable of detecting analytes containing aldehyde and ketone groups. The dyes contain nucleophilic hydrazinyl appendages and are capable of binding and detecting analytes in situ.

8 Claims, 3 Drawing Sheets

FLUOROGENIC HYDRAZINE-SUBSTITUTED COMPOUNDS

RELATED APPLICATIONS

This application is a national phase application under 35 U.S.C. §371 of International Patent Application No. PCT/US09/031830, filed Jan. 23, 2009, which claims the benefit of U.S. Provisional Application No. 61/023,191, filed Jan. 24, 2008, the disclosure of which is incorporated herein by reference in its entirety.

FIELD OF THE INVENTION

Schiff base-forming fluorogenic dyes containing a hydrazinyl substituent appended to a fluorophore are disclosed. The compounds are useful in the detection of analytes containing aldehyde and ketone groups.

BACKGROUND OF THE INVENTION

A myriad of biomarkers containing aldehyde and ketone moieties exist and can play an important role in the biological, forensic, medical and industrial sciences. In particular, aldehydes and ketones are known to be key end products in the degradation of a variety of biological molecules, such as, lipids, nucleic acids, carbohydrates and proteins. In a number of instances, these end products are a result of oxidative stress. In one example, malondialdehyde and 4-hydroxynonenal are markers for lipid peroxidation.

A number of reagents for the detection of aldehyde and ketone-containing moieties have been proposed, however, each with limited success. Among the most widely used of such reagents are dansyl hydrazine, fluorescein thiosemicarbazide, various biotin hydrazides, biotin hydroxylamine (ARP), and various aromatic amines (2-aminopyridine, 8-aminonaphthalene-1,3,6-disulfonic acid, 1-aminopyrene-3,6,8-trisulfonic acid, 2-aminoacridone). Unfortunately, these reagents require additional purification and/or secondary reagents.

Existing methods of labeling carbohydrates that utilize hydrazine, hydroxylamine and amine derivatization reagents have focused on labeling aldehydes present in, or introduced into, carbohydrates, particularly the so-called "reducing sugars". Aldehydes are typically introduced into carbohydrates by periodate oxidation. The adduct formed with the reducing sugar can be further stabilized by treatment with borohydride or a cyanoborohydride. The derivatization reaction typically proceeds or is followed by a separation technique such as chromatography, electrophoresis, precipitation, affinity isolation or other means before direct or indirect detection of the labeled product. Unlike the foregoing, which require purification and the use of a secondary detection reagent, the reagents of the present invention permit rapid in-situ detection of aldehyde and ketone moieties upon contact.

U.S. Pat. No. 6,967,251 (Haugland et al.) describes aniline-substituted quinazolinone compounds which can display fluorescent changes upon binding of aldehyde-containing compounds in a gel. However, the aniline-substituted quinazolinone core, which is important for binding of the analyte, is less fluorescent and fluorogenic than the compounds of the present invention. Accordingly, the present invention provides substantial advantages over the previously described aldehyde and ketone detector compounds.

A family of hydrazinyl substituted xanthene dyes have been previously described in U.S. Pat. No. 4,420,627 (Widiger). However, each of the xanthene moieties in Widiger are substituted to prevent analyte binding of the molecule. Particularly, the terminal nitrogen atom in the hydrazinyl moiety in Widiger is carbonylated, such that the hydrazinyl group is not nucleophilic and unable to bind an aldehyde or ketone moiety. Accordingly, the compounds are not functional in the analyte detection method of the present invention, which involve a quenched molecule up until the analyte binding event. Accordingly, the compounds in Widiger are functionally and structurally very different from those of the present invention.

SUMMARY OF THE INVENTION

The present invention provides hydrazinyl-substituted compounds capable of binding aldehyde and ketone-containing analytes in a solution, wherein upon binding of the analyte, the hydrazinyl-substituted compounds become highly fluorescent, thereby indicating the presence of the analyte.

One aspect of the invention provides a compound of Formula I:

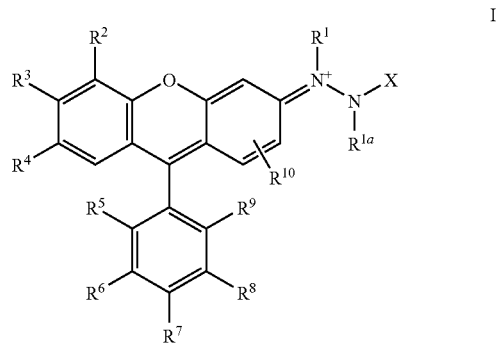

or a stereoisomer, tautomer, hydrate, solvate, or salt thereof;

wherein,

X is H or an analyte;

$R^1$ and $R^{1a}$ are independently selected from the group consisting of H, alkyl and substituted alkyl;

$R^2$, $R^4$, $R^5$, $R^6$, $R^7$, $R^8$, $R^9$ and $R^{10}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^3$ is selected from the group consisting of alkoxy, substituted alkoxy, amino, substituted amino, hydrazinyl, substituted hydrazinyl, analyte substituted hydrazinyl, alkyl, substituted alkyl, acyl, acylamino, acyloxy, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or $R^2$ and $R^3$, $R^3$ and $R^4$, or $R^2$, $R^3$ and $R^4$ are taken together to form a fused heterocyclyl group, a fused substituted heterocyclyl group, a fused aryl group, a fused substituted aryl group, a fused heteroaryl group or a fused substituted heteroaryl group.

Another aspect of the invention provides a compound of Formula II:

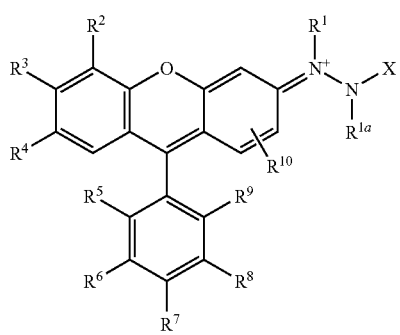

or a stereoisomer, tautomer, hydrate, solvate, or salt thereof;
wherein,
X is H or an analyte;
Y is H or an analyte;
L is —NH— or a covalent bond;
$R^1$ is selected from the group consisting of H, alkyl and substituted alkyl;
$R^2$, $R^4$, $R^5$, $R^6$, $R^7$, $R^8$, $R^9$ and $R^{10}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
$R^{11}$ is selected from the group consisting of H, alkyl, substituted alkyl, aryl, substituted aryl, heteroaryl, substituted heteroaryl, heterocyclyl, substituted heterocyclyl, cycloalkyl, and substituted cycloalkyl.

Another aspect of the invention provides a compound of Formula III:

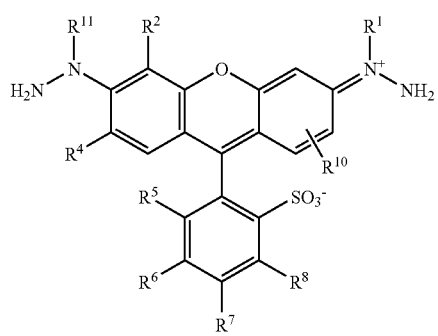

or a stereoisomer, tautomer, hydrate, solvate, or salt thereof;
wherein,
$R^1$ is selected from the group consisting of H, alkyl and substituted alkyl;

$R^2$, $R^4$, $R^5$, $R^6$, $R^7$, $R^8$ and $R^{10}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
$R^{11}$ is selected from the group consisting of H, alkyl, substituted alkyl, aryl, substituted aryl, heteroaryl, substituted heteroaryl, heterocyclyl, substituted heterocyclyl, cycloalkyl, and substituted cycloalkyl.

Another aspect of the invention provides a compound selected from the group consisting of:

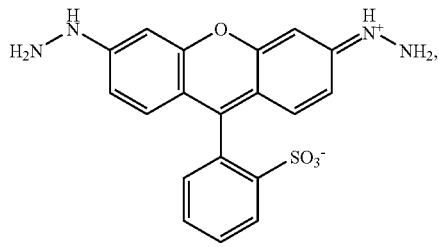

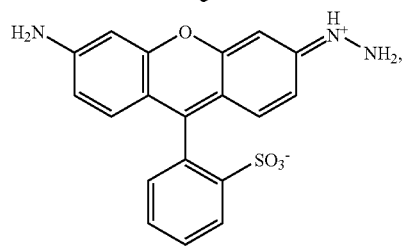

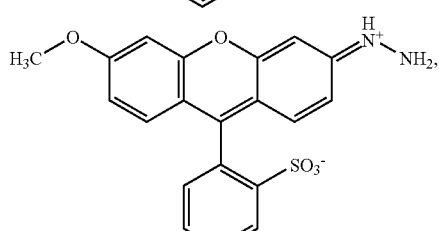

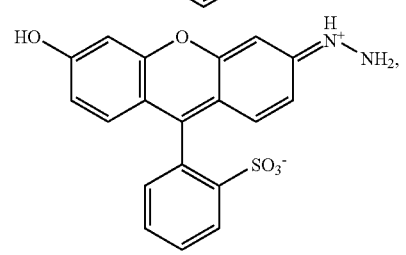

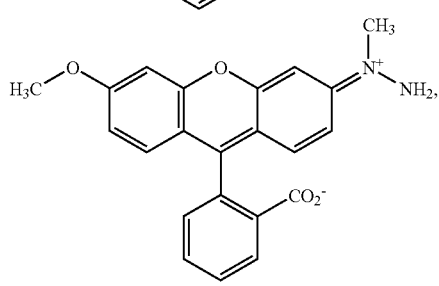

-continued

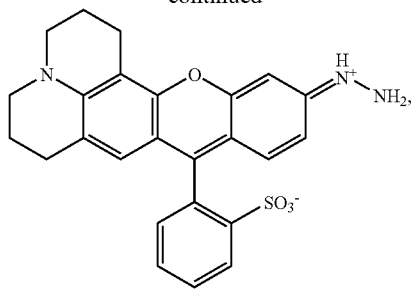

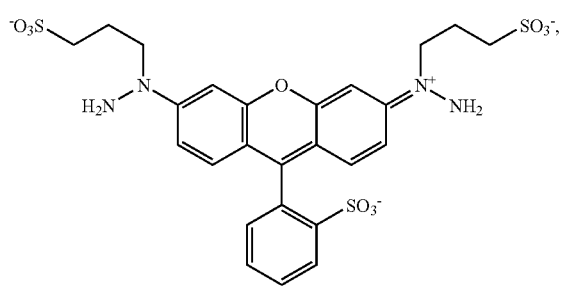

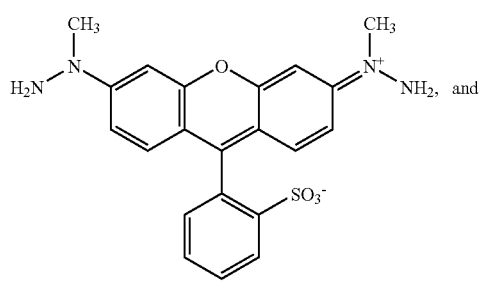

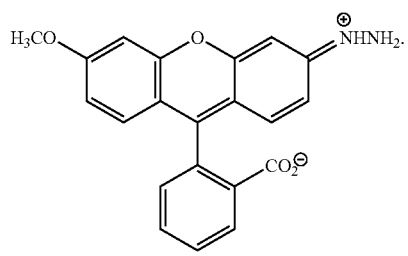

Another embodiment of the invention provides a compound selected from the group consisting of:

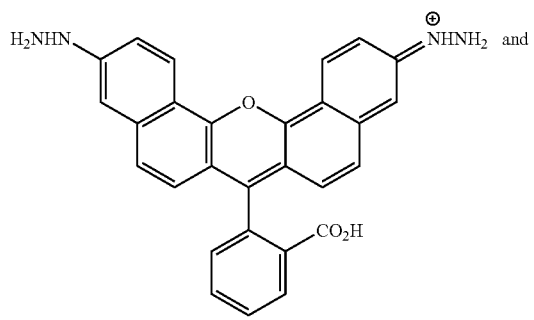

-continued

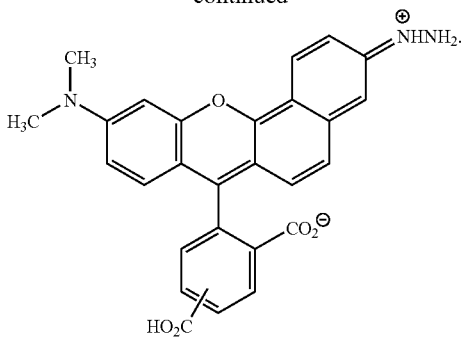

Another aspect of the invention provides a compound of Formula V:

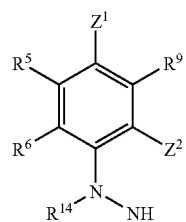

V or a stereoisomer, tautomer, hydrate, solvate, or salt thereof;

wherein,

X is H or an analyte;

$Z^1$ a fluorophore and $Z^2$ is $R^8$; or $Z^1$ is $R^8$ and $Z^2$ is a fluorophore;

$R^5$, $R^6$, $R^8$ and $R^9$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^{14}$ is selected from the group consisting of H, alkyl, substituted alkyl, aryl, substituted aryl, heteroaryl, substituted heteroaryl, heterocyclyl, substituted heterocyclyl, cycloalkyl, and substituted cycloalkyl; or X and $R^{14}$ are taken together to form a fused heterocyclyl group, substituted fused heterocycly group, fused heteroaryl group, or substituted fused heteroaryl group.

Another aspect of the invention provides a compound of Formula VI:

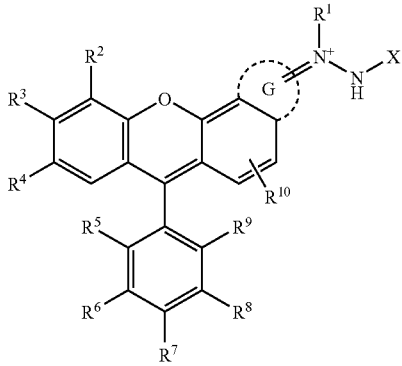

or a stereoisomer, tautomer, hydrate, solvate, or salt thereof;
wherein,
G is a 5-6 membered fused aryl or heteroaryl group;
X is H or an analyte;
$R^1$ is selected from the group consisting of H, alkyl and substituted alkyl;
$R^2$, $R^4$, $R^5$, $R^6$, $R^7$, $R^8$, $R^9$ and $R^{10}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
$R^3$ is selected from the group consisting of alkoxy, substituted alkoxy, amino, substituted amino, hydrazinyl, substituted hydrazinyl, analyte substituted hydrazinyl, alkyl, substituted alkyl, acyl, acylamino, acyloxy, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or
$R^2$ and $R^3$, $R^3$ and $R^4$, or $R^2$, $R^3$ and $R^4$ are taken together to form a fused heterocyclyl group, a fused substituted heterocyclyl group, a fused aryl group, a fused substituted aryl group, a fused heteroaryl group or a fused substituted heteroaryl group.

Another aspect of the invention provides a composition comprising:
(a) an analyte; and
(b) a compound as described herein.

Another aspect of the invention provides a method for determining the presence of an analyte of interest in a sample, wherein the method comprises:
contacting the sample with a compound described herein;
incubating the sample and the compound for a sufficient amount of time to form a complex between the compound and analyte;
illuminating the complex with an appropriate wavelength to form an illuminated complex; and
detecting emissions from the illuminated complex.

Another aspect of the invention provides a kit for detecting an analyte in a sample, wherein the kit comprises:
a compound as describe herein that binds the analyte; and
instructions for detecting the analyte.

Another aspect of the invention provides a compound comprising a (9-phenyl-3H-xanthen-3-ylidene)hydrazine, wherein the hydrazine group is unsubstituted or substituted with an analyte.

Another aspect of the invention provides a method of synthesizing a compound of Formula III, a tautomer thereof, a stereoisomer thereof, or a salt thereof:

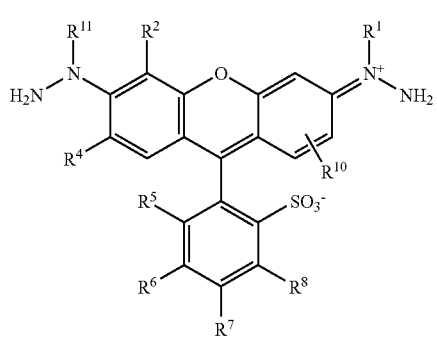

or a stereoisomer, tautomer, hydrate, solvate, or salt thereof;
wherein,
$R^1$ and $R^{11}$ are each independently selected from the group consisting of H, alkyl, substituted alkyl, aryl, substituted aryl, heteroaryl, substituted heteroaryl, heterocyclyl, substituted heterocyclyl, cycloalkyl, and substituted cycloalkyl;
$R^2$, $R^4$, $R^5$, $R^6$, $R^7$, $R^8$ and $R^{10}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;
the method comprising:
contacting a compound of formula IV:

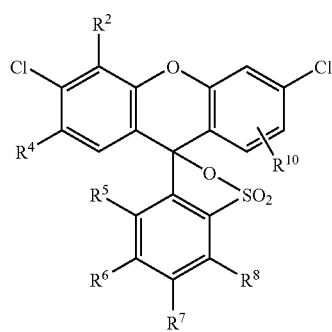

with $R^1$—NH—NH—$R^{12}$ and $R^{11}$—NH—NH—$R^{12}$, wherein $R^{12}$ is a protecting group, thereby obtaining a compound of Formula III(a):

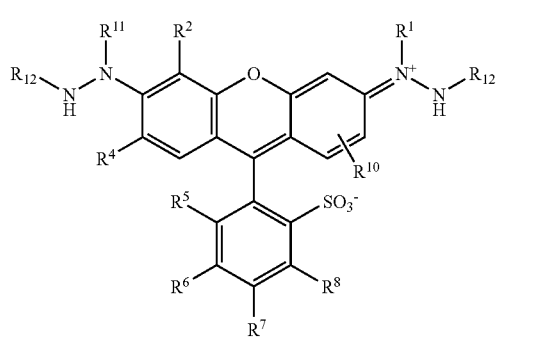

contacting $R^{12}$ with a deprotecting reagent, thereby obtaining a compound of Formula III.

In another embodiment the $SO_3^-$ group in formula III is a $CO_2^-$ and the $SO_2$ group is a CO.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Introduction

Figure 1:
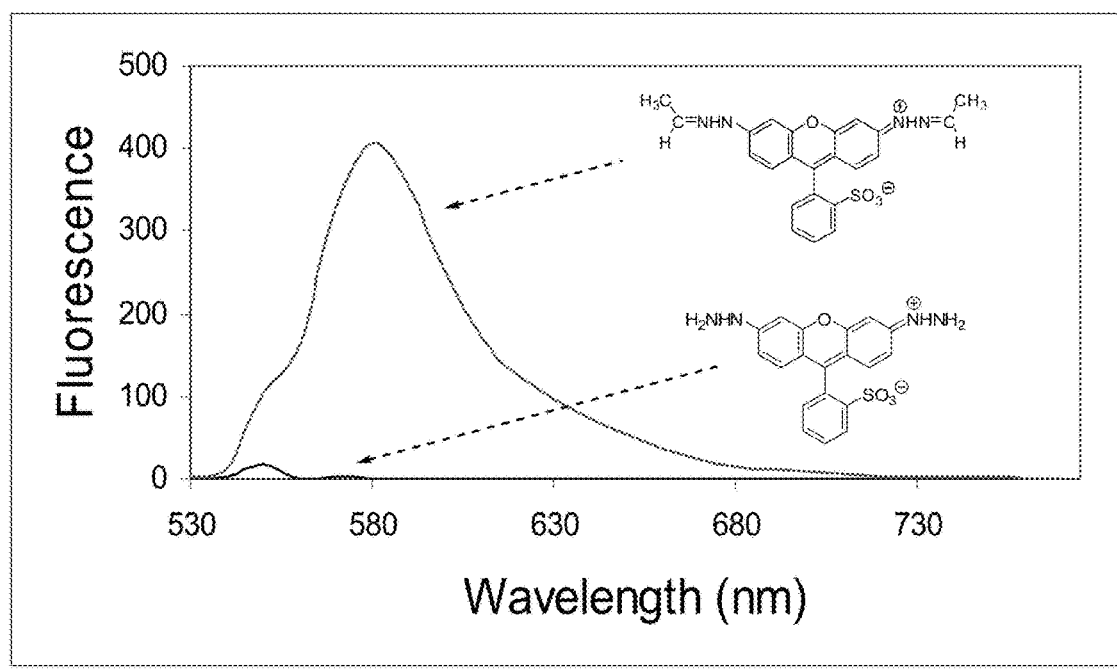
FIG. 1 shows emmision spectra of 2-(6-hydrazinyl-3-hydrazono-3H-xanthen-9-yl)benzenesulfonate before and after contact with acetaldehyde. There was a significant fluorescent increase upon reaction with an aldehyde. Spectra were taken at pH 6 in a 50 mM phosphate buffer solution.
Figure 2:
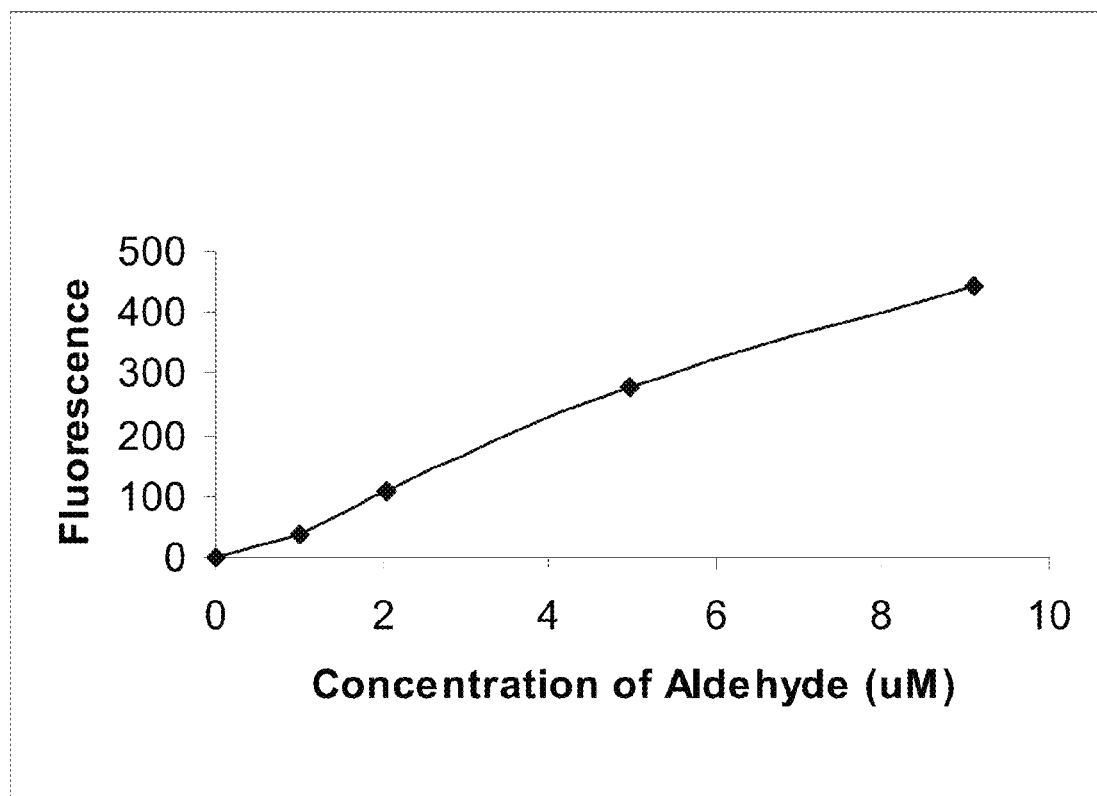
FIG. 2 shows quantitation of aldehyde content in solution. 20 uM of 2-(6-hydrazinyl-3-hydrazono-3H-xanthen-9-yl)benzenesulfonate was incubated with aldehyde for 15 min at room temperature at pH 6 in a 50 mM phosphate buffer solution.

The present invention provides compounds with a hydrazine appendage capable of binding aldehyde and ketone groups present on analytes of interest. The compounds of the present invention generally have a fluorescent core that is quenched in the unbound state. Once the hydrazine reacts with an aldehyde or ketone, a Schiff base (imine) is formed. The resultant compound is highly fluorescent, thereby providing an excellent method for detection of aldehydes and ketones in solution.

The compounds of the present invention provide distinct advantages over known aldehyde detection reagents, including being fluorogenic with a high quantum yield, unique emission and excitation wavelengths outside the range of endogenous particles, highly stable and high specificity for ketones and aldehydes, soluble in a variety of solutions, particularly aqueous solutions, and compatibility with biological applications. Additionally, reaction with the compounds of the present invention proceeds under milder conditions (rt, aqueous acetic acid) than existing assays. Furthermore, the Schiff base formation appears to be a near-instantaneous reaction, whereas existing assays require at least 1 hour reaction time at elevated temperatures. Additionally, the available wavelength range for the compounds is large and tunable.

DEFINITIONS

Before describing the present invention in detail, it is to be understood that this invention is not limited to specific compositions or process steps, as such may vary. It should be noted that, as used in this specification and the appended claims, the singular form "a", "an" and "the" include plural references unless the context clearly dictates otherwise. Thus, for example, reference to "a hydrazine group" includes a plurality of hydrazine groups and reference to "an analyte" includes a plurality of analytes and the like.

Unless defined otherwise, all technical and scientific terms used herein have the same meaning as commonly understood by one of ordinary skill in the art to which this invention is related. The following terms are defined for purposes of the invention as described herein.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups —NRC(O)alkyl, —NRC(O)substituted alkyl, —NRC(O)cycloalkyl, —NRC(O)substituted cycloalkyl, —NRC(O)cycloalkenyl, —NRC(O)substituted cycloalkenyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic wherein R is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —$NH_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cylcoalkyl, —$SO_2$-cycloalkenyl, —$SO_2$-substituted cylcoalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' nor R" are hydrogen.

"Aminocarbonyl" refers to the group —C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group —C(S)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonylamino" refers to the group —NRC(O)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —NRC(S)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonyloxy" refers to the group —O—C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group —SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group —O—SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonylamino" refers to the group —NR—SO$_2$NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkyenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkyenyl, aryl, substituted aryl, heteroaryl, substituted heteroaryl, heterocyclic and substituted heterocyclic are as defined herein.

"Amidino" refers to the group —C(=NR''')R'R" where R', R", and R''' are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified, for example, by vinyl, allyl, and but-3-en-1-yl.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy substitution is not attached to a vinyl (unsaturated) carbon atom.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy substitution is not attached to an acetylenic carbon atom.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —NR—C(O)O-alkyl, substituted —NR—C(O)O-alkyl, —NR—C(O)O-alkenyl, —NR—C(O)O-substituted alkenyl, —NR—C(O)O-alkynyl, —NR—C(O)O-substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic wherein R is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, substituted —O—C(O)O-alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH$_2$.

"Substituted guanidino" refers to —NR$^{13}$C(=NR$^{13}$)N(R$^{13}$)$_2$ where each R$^{13}$ is independently selected from the group consisting of hydrogen, alkyl, substituted alkyl, aryl, substituted aryl, heteroaryl, substituted heteroaryl, heterocyclic, and substituted heterocyclic and two R$^{13}$ groups attached to a common guanidino nitrogen atom are optionally joined together with the nitrogen bound thereto to form a heterocyclic or substituted heterocyclic group, provided that at least one R$^{13}$ is not hydrogen, and wherein said substituents are as defined herein.

"H" indicates hydrogen.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or unsaturated group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzob]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Hydrazinyl" refers to the group —NHNH$_2$—, =NNH—, or =N$^{(+)}$HNH$_2$—.

"Substituted hydrazinyl" refers to a hydrazinyl group, wherein a non-hydrogen atom, such as an alkyl group, is appended to one or both of the hydrazinyl amine groups. An example of substituted hydrazinyl is —N(alkyl)-NH$_2$ or =N$^+$(alkyl)-NH$_2$.

"Nitro" refers to the group —NO$_2$.

"Oxo" refers to the atom (=O) or (—O$^-$).

"Spirocyclyl" refers to divalent saturated cyclic group from 3 to 10 carbon atoms having a cycloalkyl or heterocyclyl ring with a spiro union (the union formed by a single atom which is the only common member of the rings) as exemplified by the following structure:

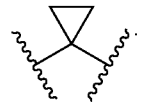 [SMILES: *C1(*)CC1 ; "."]

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cylcoalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thiol" refers to the group —SH.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

A dashed line projecting from a substituent, such as:

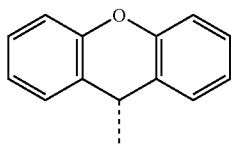

indicates the point of attachment to the base molecule. For a fused ring, dashed lines indicate portions of the base molecule where the fused ring is attached, such as:

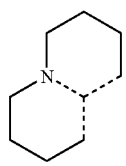

wherein the full molecule could have the structure:

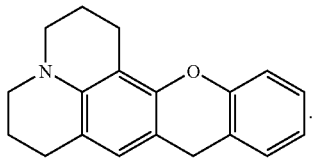 [SMILES: c1ccc2c(c1)Cc1cc3c4c(c1O2)CCCN4CCC3]

"Stereoisomer" or "stereoisomers" refer to compounds that differ in the chirality of one or more stereocenters. Stereoisomers include enantiomers and diastereomers.

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N-moeity such as pyrazoles, imidazoles, benzimidazoles, triazoles, and tetrazoles.

"Patient," "subject" or "individual" refers to mammals and includes humans and non-human mammals, such as monkeys, dogs, cats, horses, cows, pigs or rats.

"Salt" refers to acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

The terms "protein" and "polypeptide" are used herein in a generic sense to include polymers of amino acid residues of any length. The term "peptide" is used herein to refer to polypeptides having less than 250 amino acid residues, typically less than 100 amino acid residues. The terms apply to amino acid polymers in which one or more amino acid residues are an artificial chemical analogue of a corresponding naturally occurring amino acid, as well as to naturally occurring amino acid polymers.

The term "reactive group" as used herein refers to a group that is capable of reacting with another chemical group to form a covalent bond, i.e. is covalently reactive under suitable reaction conditions, and generally represents a point of attachment for another substance. The reactive group is a moiety, such as carboxylic acid or succinimidyl ester, on the compounds of the present invention that is capable of chemically reacting with a functional group on a different compound to form a covalent linkage. Reactive groups generally include nucleophiles, electrophiles and photoactivatable groups.

Exemplary reactive groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds., *Organic Functional Group Preparations*, Academic Press, San Diego, 1989).

The term "detectable response" as used herein refers to an occurrence of or a change in, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of the above parameters.

The term "dye" as used herein refers to a compound that emits light to produce an observable detectable signal.

The term "fluorophore" or "fluorogenic" as used herein refers to a composition that demonstrates a change in fluorescence upon binding to a biological compound or analyte interest. Preferred fluorophores of the present invention include fluorescent dyes having a high quantum yield in aqueous media. Exemplary fluorophores include xanthene, indole, borapolyazaindacene, furan, and benzofuran, among others. The fluorophores of the present invention may be substituted to alter the solubility, spectral properties or physical properties of the fluorophore.

The term "carrier molecule" as used herein refers to a biological or a non-biological component that is covalently bonded to a compound of the present invention. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. "Covalently bonded" as used herein indicates a direct covalent linkage or through a number of atoms corresponding to a linker moiety.

The term "Linker" as used herein, refers to a single covalent bond or a series of stable covalent bonds incorporating 1-20 nonhydrogen atoms selected from the group consisting of C, N, O, S and P that covalently attach the fluorogenic or fluorescent compounds to another moiety such as a chemically reactive group or a biological and non-biological component. Exemplary linking members include a moiety that includes —C(O)NH—, —C(O)O—, —NH—, —S—, —O—, and the like. A "cleavable linker" is a linker that has one or more cleavable groups that may be broken by the result of a reaction or condition. The term "cleavable group" refers to a moiety that allows for release of a portion, e.g., a fluorogenic or fluorescent moiety, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., *Biochem. Biophys. Acta*, 761: 152-162 (1983); Joshi et al., *J. Biol. Chem.*, 265: 14518-14525 (1990); Zarling et al., *J. Immunol.*, 124: 913-920 (1980); Bouizar et al., *Eur. J. Biochem.*, 155: 141-147 (1986); Park et al., *J. Biol. Chem.*, 261: 205-210 (1986); Browning et al., *J. Immunol.*, 143: 1859-1867 (1989). Moreover a broad range of cleavable, bifunctional (both homo- and hetero-bifunctional) spacer arms are commercially available.

An exemplary cleavable group, an ester, is cleavable group that may be cleaved by a reagent, e.g. sodium hydroxide, resulting in a carboxylate-containing fragment and a hydroxyl-containing product.

The linker can be used to attach the compound to another component of a conjugate, such as a targeting moiety (e.g., antibody, ligand, non-covalent protein-binding group, etc.), an analyte, a biomolecule, a drug and the like.

Unless indicated otherwise, the nomenclature of substituents that are not explicitly defined herein are arrived at by naming the terminal portion of the functionality followed by the adjacent functionality toward the point of attachment. For example, the substituent "arylalkyloxycabonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., a methyl substituted with 5 fluoro groups). Such impermissible substitution patterns are well known to the skilled artisan.

A simple, sensitive reagent for the selective detection of aldehydes/ketones is a useful tool for high-throughput screening systems in chemistry and biology. In particular, aldehydes have been widely known as among the key end products from a degradation of a variety of biological molecules, e.g. lipids, nucleic acids, carbohydrates, proteins, induced by oxidative stress.

Malondialdehyde (MDA) is a major lipid peroxidation product. The present invention involves reaction of non-fluorescent (or virtually non-fluorescent) fluorophore-hydrazines with MDA under mild conditions such that a fluorescent pyrazole is formed. Thus a fluorogenic assay for lipid peroxidation is presented that allows for a large wavelength range to be utilized.

Lipid peroxidation is a major indicator of oxidative stress. Researchers need to measure lipid peroxidation in many types of samples including drugs, food products, and human and biological tissue. The extent of lipid peroxidation provides important information regarding free radical activity in disease states, and it also provides a measure of antioxidant activity of potential therapeutic compounds. Malondialdehyde (MDA) is a key lipid peroxidation product. The most commonly used assay of lipid peroxidation involves the reaction of MDA with 2 equivalents of thiobarbituric acid, aka the OXI-TEK TBARS Assay Kit. The resulting oxonol product is detected by absorbance or fluorescence (e.g. Janero D., "Malondialdehyde and thiobarbituric acid reactivity as diagnostic indices of lipid peroxidation and peroxidative tissue injury," *Free Radical Biology & Medicine*, 1998, 9: 515-40). Drawbacks to this method include: 1) samples must be heated in strong acetic acid for 1 hour at 95° C.; 2) only a single wavelength set (530 nm excitation/550 nm emission) is produced.

MDA is known to react with aryl hydrazines to form pyrazoles (Otteneder et al, "Reaction of Malondialdehyde-DNA adducts with Hydrazines-Development of a Facile Assay for Quantification of Malondialdehyde Equivalents in DNA," *Chem. Res. Toxicol.* 2002, 15: 312-8).

The present invention describes a new class of fluorogenic dyes for the detection and quantitation of aldehyde/ketone functional groups. The compounds are capable of reacting with a variety of analytes, such as malondialdehyde (MDA) as shown below:

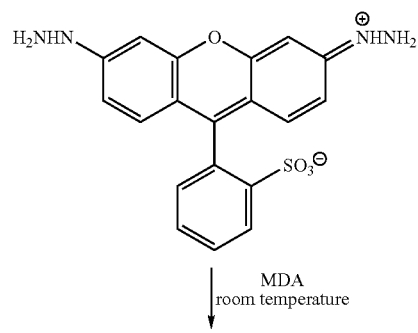

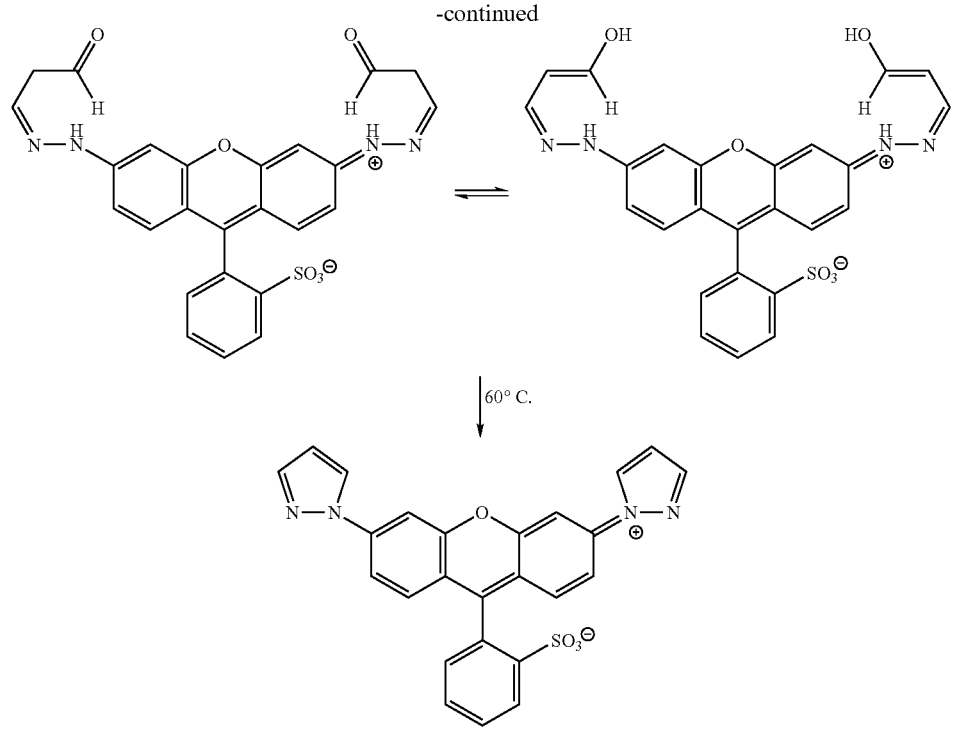

Aniline versions of visible wavelength fluorophores such as fluoresceinamine, 5-amino-tetramethylrhodamine, and 8-aminophenyl-BODIPY are virtually non-fluorescent because of internal charge transfer (ICT). During the fluorophore excited state, the LUMO is filled by intramolecular transfer of electron density from the aniline nitrogen electron lone pair. This filling precludes relaxation to the ground state via fluorescence. Thus, even though the compounds absorb visible light, they do not fluoresce as they return to the ground state. These compounds can be made fluorescent by conversion into products in which the aniline nitrogen electron lone pair becomes unavailable for ICT. In one embodiment, the present invention involves reaction of fluorophore-hydrazine combinations (non-fluorescent because of ICT) with MDA to form fluorescent pyrazole products. The pyrazole products are fluorescent because the electron lone pair on the "first" nitrogen atom of the hydrazine moiety becomes part of the aromaticity of the pyrazole, i.e. this electron lone pair is no longer available to quench fluorescence by ICT.

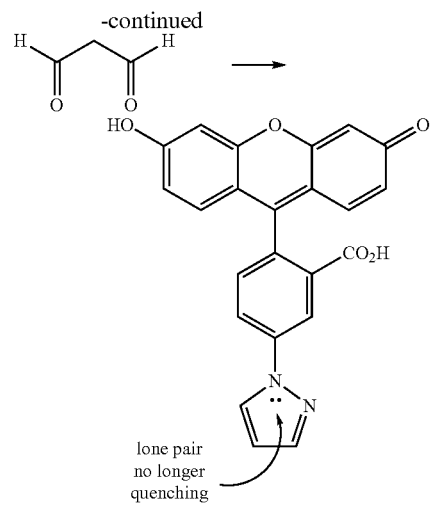

This principle can be applied to a number of other fluorophore hydrazine combinations, for example:

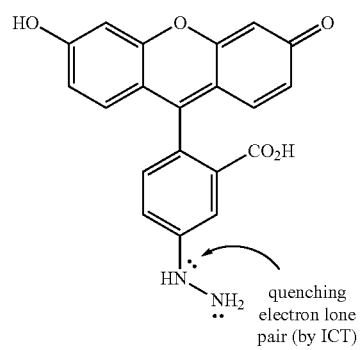

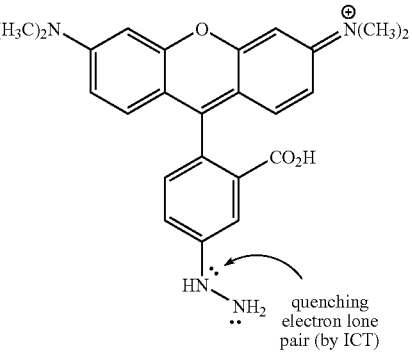

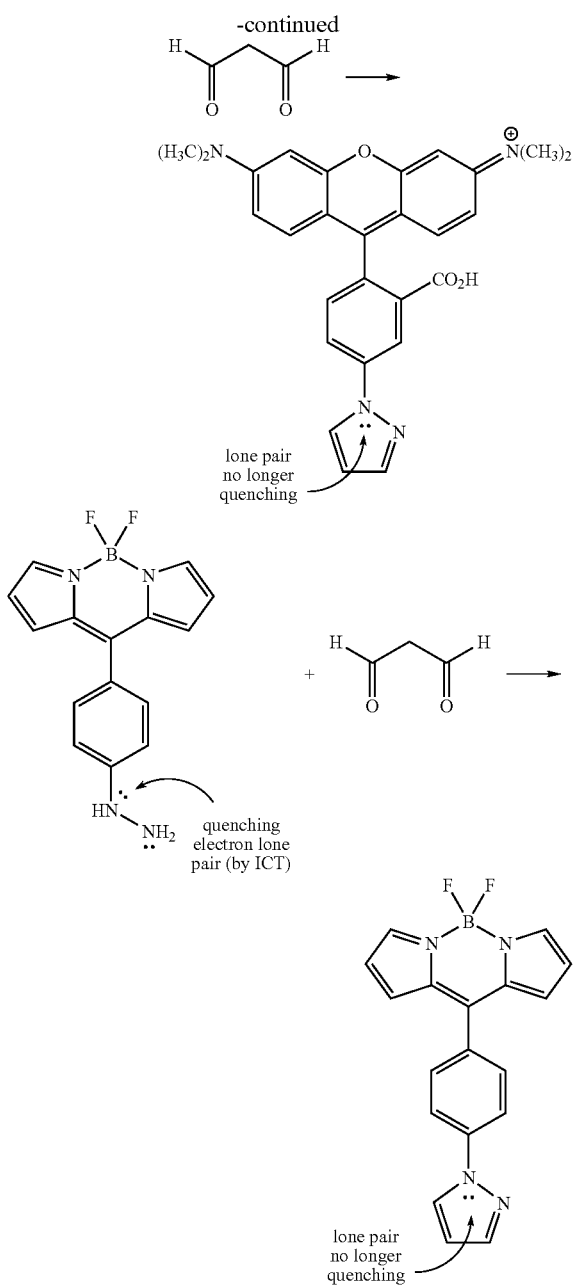

The aldehyde or ketone functional group is typically naturally present on the analyte prior to its conjugation to the reagent of the invention. Alternatively, the aldehyde or ketone functionality is formed on the target substance by chemical, light, heat, radiation, or enzymatic treatment prior to reaction with a reagent of the invention. In one aspect of the invention, the target substance is treated with an oxidizing condition, such as a chemical oxidizing agent (for example a periodate, a strong acid, or ozone), oxidizing radiation, photolysis, or enzymatic oxidation.

Where they are not present, aldehydes and ketones are also introduced into molecules using extrinsic reagents that already contain an aldehyde or ketone. For instance, aldehydes are introduced at aliphatic amine sites with the reagents succinimidyl 4-formylbenzoate or succinimidyl 4-formylphenoxyacetate (Molecular Probes, Eugene Oreg.). These reagents selectively modify proteins on the surface of live cells, and thereby permit the analysis of the topology of peptide and protein exposure on cells surfaces following, for instance, lysis and gel electrophoresis. Additionally, galactosides are enzymatically transferred to a target carbohydrate using UDP-galactose:N-acetylglucosamine galactosyltransferase and, following galactose oxidase-catalyzed oxidation to an aldehyde (as described by Shaper et al. J. SUPRAMOL. STRUCTURE 6, 291-299 (1977)), the target carbohydrate can be modified by a reagent of the invention. Glycoproteins such as horseradish peroxidase are oxidized to aldehydes and their conjugates subsequently used in various detection schemes according to the instant invention The oligosaccharide components of cell surface glycoproteins play a role in the interactions that regulate many important biological processes, from cell-cell adhesion to signal transduction. Sialic acids are the most abundant terminal components of oligosaccharides on mammalian cell-surface glycoproteins and are synthesized from the six-carbon precursor N-actylmannosamine. When cells in culture are incubated with N-levulinoyl-D-mannosamine, this ketone-containing monosaccharide serves as a substrate in the oligosaccharide synthesis pathway, resulting in ketone-tagged cell-surface oligosaccharides (as described in U.S. Pat. No. 6,075,134 to Bertozzi et al. (2000), incorporated by reference). If these tagged cells are then labeled with a reagent of the invention, they are readily identified or traced using either by imaging or flow cytometry.

The conjugated target is typically a peptide, a protein, a nucleoside, a nucleotide, an oligonucleotide, a nucleic acid, a sugar, a polysaccharide, a lipid, a lipopolysaccharide, a ganglioside, a drug, a hormone, or a ligand having a molecular weight less than 2,000 Daltons. Preferably, the conjugated target is a protein, a nucleic acid, a lipid, a lipopolysaccharide, a ganglioside, a drug, or a hormone.

The use of the invention to label aldehyde- and ketone-containing target substances comprises combining a reagent of the present invention with a sample that contains or is thought to contain a desired target, incubating the mixture of reagent and sample for a time sufficient for the reagent to form a covalent conjugate with the target substance in the sample, such that the conjugate exhibits a detectable fluorescent signal.

The characteristics of the resulting reagent-target conjugate, including the presence, location, intensity, excitation and emission spectra, fluorescence polarization, fluorescence lifetime, photobleaching rate and other physical properties of the fluorescent signal can be used to detect, differentiate, sort, quantitate, and/or analyze aspects or portions of the sample. The reagents of the invention are optionally used in conjunction with one or more additional detection reagents (preferably having detectably different fluorescence characteristics).

Selected Target Substances Containing Aldehydes or Ketones Formaldehyde Acetone Benzaldehydes Reducing sugars and polysaccharides in ring-opened forms Steroids Keto acids Aldehyde- or ketone-containing drugs Aldehyde- or ketone-containing environmental pollutants Aldehyde- or ketone-containing organics Acid-treated deoxyribonucleic acids Oxidized sugars Oxidized polysaccharides Oxidized glycols Oxidized glycoproteins Oxidized glycolipids Oxidized glycosaminoglycans Oxidized ribonucleic acids Oxidized biological cells Oxidized N-terminal serine residues of proteins Oxidized N-terminal threonine residues of proteins Typically, when the reagent of the invention is used in the form of a staining solution, preferably an aqueous or aqueous miscible solution that is compatible with the sample and the intended use. For biological samples, where minimal perturbation of cell morphology or physiology is desired, the staining solution is selected accordingly. For solution assays, the staining solution preferably does not perturb the native conformation of the target substance.

Although typically used in an aqueous or aqueous miscible solution, the staining solution is typically prepared by first dissolving the reagent in a water-miscible organic solvent such as dimethylsulfoxide (DMSO), dimethylformamide (DMF), or a lower alcohol, such as methanol or ethanol. This stock solution is typically prepared at a concentration of greater than about 50-times that used in the final staining solution, then diluted one or more times with an aqueous solvent or a buffer solution such that the reagent is present in an effective amount. Typically, the reagent is first dissolved in 100% DMF, and then diluted with buffer. The staining solution optionally further comprises additional formulation components, such as acids, buffering agents, inorganic salts, polar organic solvents, antioxidants, and ion chelators.

The pH of the staining solution is optionally modified by the inclusion of a buffering agent. Any buffering agent that is compatible with the target substance in the sample is suitable for inclusion in the staining solution. In a preferred embodiment the buffer is PBS. In another embodiment, the buffering agent is one of the so-called "Good's" buffers. "Good's" buffers include BES (N,N-bis[2-hydroxyethyl]-2-aminoethanesulfonic acid; 2-[bis(2-hydroxyethyl)amino]ethanesulfonic acid), BICINE (N,N-bis[2-hydroxyethyl]glycine), CAPS (3-[cyclohexylamino]-1-propanesulfonic acid), EPPS (N-[2-hydroxyethyl]piperazine-N'-[3-propanesulfonic acid]), HEPES ((N-[2-hydroxyethyl]piperazine-N'-[2-ethanesulfonic acid]), MES (2-[N-morpholino]ethanesulfonic acid), MOPS (3-[N-morpholino]propanesulfonic acid), PIPES (piperazine-N,N'-bis[2-ethanesulfonic acid]; 1,4-piperazinediethanesulfonic acid), TAPS(N-tris[hydroxymethyl]methyl-3-aminopropanesulfonic acid; ([2-hydroxy-1,1-bis(hydroxymethyl)ethyl]amino-1-propanesulfonic acid), TES (N-tris[hydroxymethyl]methyl-2-aminoethanesulfonic acid; 2-([2-hydroxy-1,1-bis(hydroxymethyl)ethyl]amino)ethanesulfonic acid), or TRICINE (N-tris [hydroxymethyl]methylglycine; N-[2-hydroxy-1,1-bis(hydroxymethyl)ethyl]glycine).

Other preferred buffering agents include salts of formate, citrate, acetate, N-(2-hydroxyethyl)-N'-(2-sulfoethyl)piperazine, imidazole, N-(2-hydroxyethylpiperazine)-N'-2-ethanesulfonic acid, Tris(hydroxymethyl)aminomethane acetate, or Tris(hydroxymethyl)aminomethane hydrochloride. In a preferred embodiment, the buffering agent is MES, sodium acetate, or acetic acid, preferably acetic acid. The buffering agent or mixture of buffering agents is typically present in the staining solution at a concentration of 20 mM to 500 mM, preferably about 25 mM to about 100 mM. Where the buffering agent is acetic acid, it is preferably present in a concentration of about 1%-6%, more preferably at about 3%.

In a particularly advantageous formulation of the staining solution, the staining solution additionally comprises an inorganic salt. Advantageous inorganic salts produce staining formulations that exhibit low background signals when staining glycoproteins in electrophoretic gels. Particularly useful and inexpensive salts include sodium chloride, ammonium sulfate, magnesium chloride, magnesium acetate, zinc chloride, magnesium sulfate and magnesium glucuronate present in the staining solution at a concentration of 1-50%. In a preferred embodiment, the inorganic salt is sodium chloride or magnesium chloride, more preferably magnesium chloride.

An effective amount of reagent is the amount of reagent sufficient to give a detectable fluorescence response in combination with the desired target. The reagent concentration in the solution must be sufficient both to contact the target in the sample and to combine with the target in an amount sufficient to give a signal, but too much reagent may cause problems with background fluorescence or speckling in gels. The optimal concentration and composition of the staining solution is determined by the nature of the sample (including physical, biological, biochemical and physiological properties), the nature of the reagent-target interaction (including the transport rate of the reagent to the site of the target), and the nature of the analysis being performed, and can be determined using standard procedures, similar to those described in examples below.

In another embodiment of the invention, the target substance contains a carboxylic acid or sulfonic acid functional group, therefore the functional group must first be activated before combining with a staining solution containing a reagent of the invention, depending upon the properties of the target substance. Typically carbodiimides, such as EDAC, or dicyclohexylcarbodiimide (DCC) are used to activate carboxylic acids, whereas sulfonic acids most often require formation of their sulfonyl chloride by standard means. The reagent adducts of carboxylic acids and sulfonic acids are typically used to characterize the target substance, or the conjugates are used as fluorescent tracers. Carboxylic acid and sulfonic acids do not form stable adducts when stained in gels or solutions, thus differentiating them from aldehydes and ketones.

Particular Aspects of the Invention:

One aspect of the invention provides a compound of Formula I:

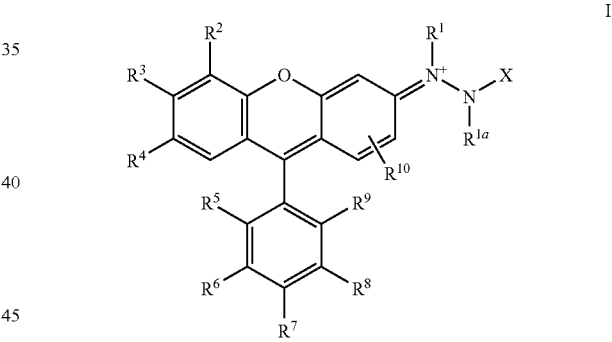

or a stereoisomer, tautomer, hydrate, solvate, or salt thereof;

wherein,

X is H or an analyte;

$R^1$ and $R^{1a}$ are independently selected from the group consisting of H, alkyl and substituted alkyl;

$R^2$, $R^4$, $R^5$, $R^6$, $R^7$, $R^8$, $R^9$ and $R^{10}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^3$ is selected from the group consisting of alkoxy, substituted alkoxy, amino, substituted amino, hydrazinyl, substituted hydrazinyl, analyte substituted hydrazinyl, alkyl, substituted alkyl, acyl, acylamino, acyloxy, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or $R^2$ and $R^3$, $R^3$ and $R^4$, or $R^2$, $R^3$ and $R^4$ are taken together to form a fused heterocyclyl group, a fused substituted heterocyclyl group, a fused aryl group, a fused substituted aryl group, a fused heteroaryl group or a fused substituted heteroaryl group.

In another embodiment, $R^1$ is H. Alternatively, $R^1$ is alkyl or substituted alkyl. In a preferred embodiment $R^{1a}$ is H. It is noted that $R^{1a}$ is not a carbonyl group since the resultant amide would not be nucleophilic nor functional as a aldehyde/ketone reactive moiety. In another embodiment, $R^3$ hydrazinyl or substituted hydrazinyl. In another embodiment, $R^3$ is methoxy. In another embodiment, $R^3$ is hydroxy. In another embodiment, $R^3$ is amino.

In another embodiment of the invention, $R^2$, $R^3$ and $R^4$ are taken together to form a fused heterocyclyl group or substituted fused heterocyclyl group of the formula:

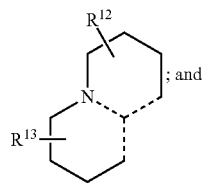

; and $R^{12}$ and $R^{13}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl.

In another embodiment, $R^4$, $R^5$, $R^6$, $R^7$, $R^8$ and $R^{10}$ are all H. In another embodiment, $R^2$, $R^4$, $R^5$, $R^6$, $R^7$, $R^8$ and $R^{10}$ are all H. In another embodiment, $R^9$ is $—SO_3^-$. In another embodiment, $R^9$ is $—CO_2^-$. In another embodiment, X is H. In another embodiment, $R^3$ is methoxy and $R^9$ is $—CO_2^-$.

In another embodiment of the invention, X is an analyte. In another embodiment, the analyte is bound through an imine. In another embodiment, the analyte is selected from the group consisting of an amino acid, a peptide, a protein, a carbohydrate, a polysaccharide, a nucleoside, a nucleotide, an oligonucleotide, a nucleic acid polymer, a drug, a lipid, and a synthetic polymer. In another embodiment, the analyte comprises a carbonyl group. In another embodiment, the analyte comprises an aldehyde group. In another embodiment, $R^3$ is analyte substituted hydrazinyl. In another embodiment, the analyte is bound through an imine. In another embodiment the analyte is malondialdehyde. In another embodiment the analyte is 4-hydroxynonenal.

Another particular aspect of the invention provides a salt of the compound.

Another aspect of the invention provides a compound of Formula II:

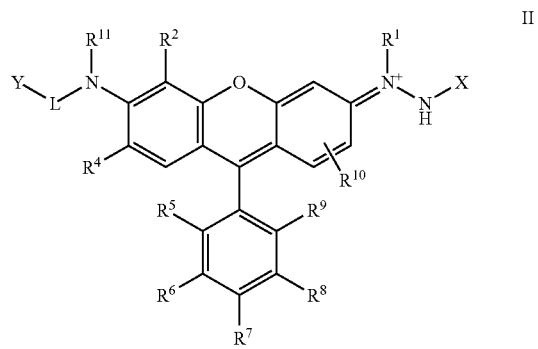

or a stereoisomer, tautomer, hydrate, solvate, or salt thereof;
wherein,
X is H or an analyte;
Y is H or an analyte;
L is —NH— or a covalent bond;
$R^1$ is selected from the group consisting of H, alkyl and substituted alkyl;
$R^2$, $R^4$, $R^5$, $R^6$, $R^7$, $R^8$, $R^9$ and $R^{10}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
$R^{11}$ is selected from the group consisting of H, alkyl, substituted alkyl, aryl, substituted aryl, heteroaryl, substituted heteroaryl, heterocyclyl, substituted heterocyclyl, cycloalkyl, and substituted cycloalkyl.

In another more particular embodiment, $R^9$ is $SO_3^-$. In another embodiment, $R^9$ is $CO_2^-$. In another embodiment, $R^2$, $R^4$, $R^5$, $R^6$, $R^7$, $R^8$ and $R^{10}$ are H. In another embodiment, $R^1$ and $R^{11}$ are H. In another embodiment, $R^1$ is alkyl or substituted alkyl and $R^{11}$ is alkyl or substituted alkyl. In another embodiment thereof, $R^1$ and $R^{11}$ are $—(CH_2)_3SO_3^-$. In another embodiment, X and Y are H. In another embodiment, X is an analyte and Y is an analyte. In another embodiment, L is —NH—. In another embodiment, L is a covalent bond.

Another aspect of the invention provides a compound of Formula III:

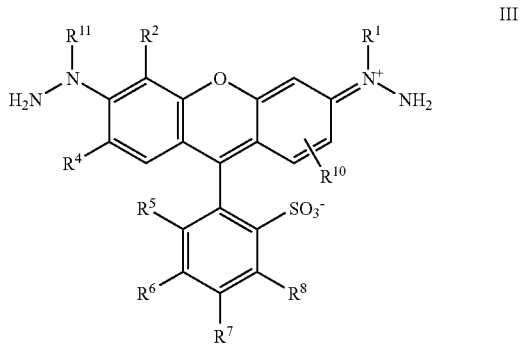

or a stereoisomer, tautomer, hydrate, solvate, or salt thereof;

wherein,

R¹ is selected from the group consisting of H, alkyl and substituted alkyl;

R², R⁴, R⁵, R⁶, R⁷, R⁸ and R¹⁰ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO₃⁻, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and R¹¹ is selected from the group consisting of H, alkyl, substituted alkyl, aryl, substituted aryl, heteroaryl, substituted heteroaryl, heterocyclyl, substituted heterocyclyl, cycloalkyl, and substituted cycloalkyl.

In a more particular embodiment thereof, R², R⁴, R⁵, R⁶, R⁷, R⁸ and R¹⁰ are hydrogen. More particularly, R¹ and R¹¹ are H. In another embodiment, R¹ is alkyl or substituted alkyl and R¹¹ is alkyl or substituted alkyl. In another embodiment, R¹ and R¹¹ are both —(CH₂)₃SO₃.

In another embodiment the SO₃⁻ group in formula III is a CO₂⁻.

Another aspect of the invention provides a compound selected from the group consisting of:

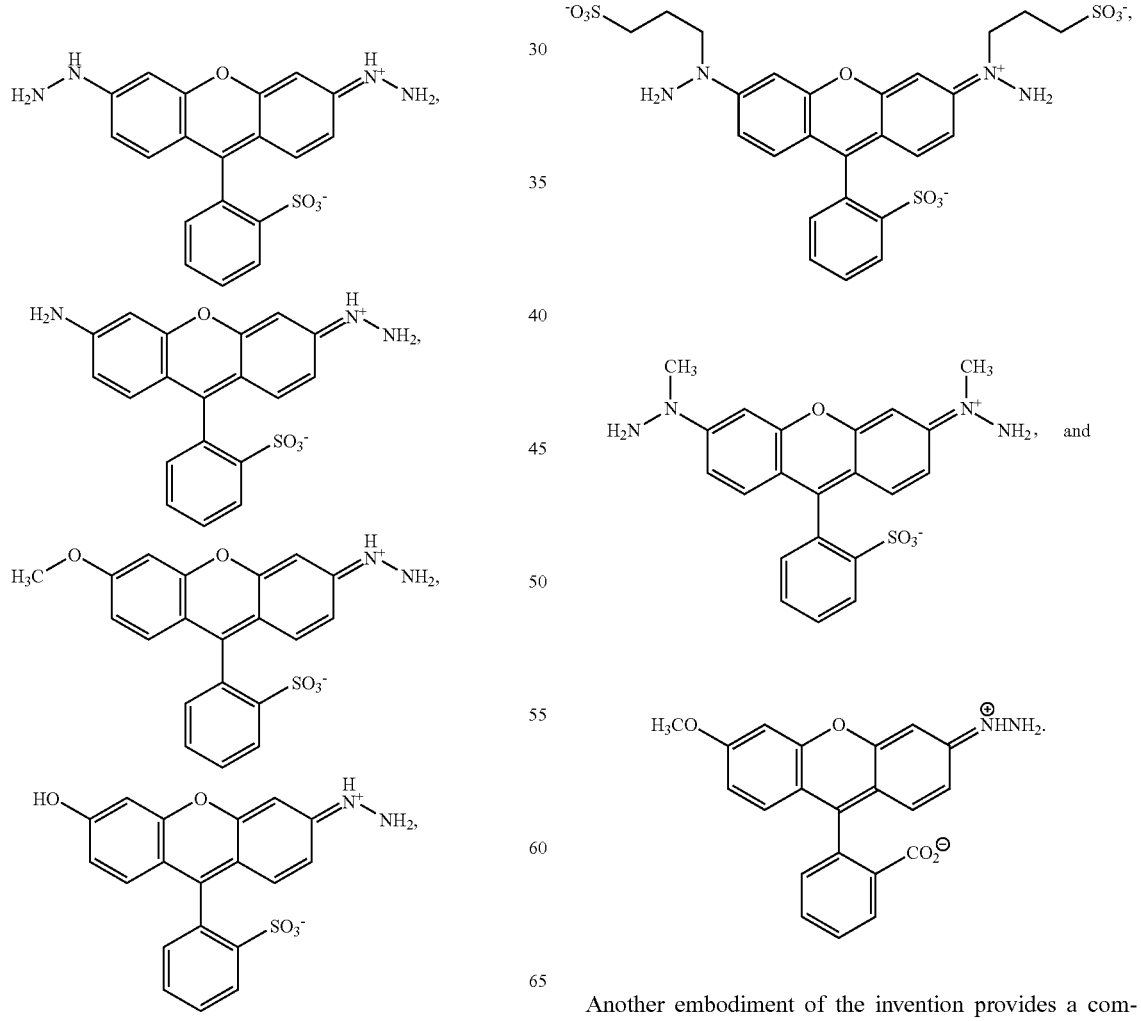

Another embodiment of the invention provides a compound selected from the group consisting of:

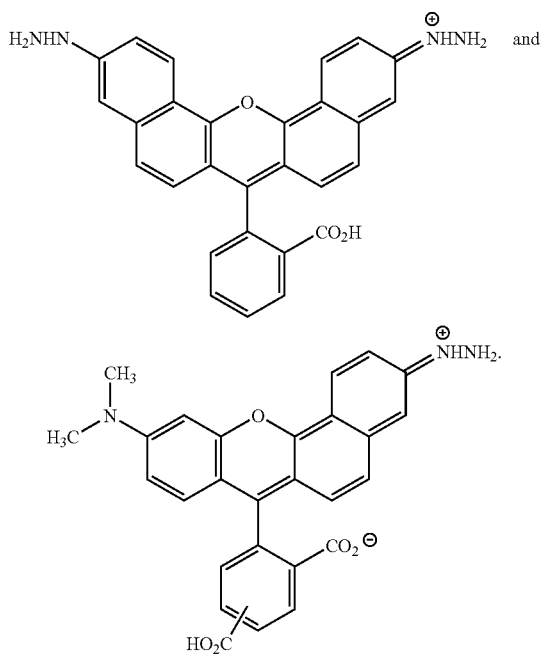

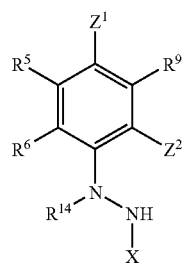

Another embodiment thereof provides a salt or tautomer thereof.

Another aspect of the invention provides a compound of Formula V:

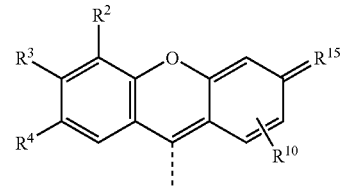

or a stereoisomer, tautomer, hydrate, solvate, or salt thereof;
wherein,
X is H or an analyte;
$Z^1$ a fluorophore and $Z^2$ is $R^8$; or
$Z^1$ is $R^8$ and $Z^2$ is a fluorophore;
$R^5$, $R^6$, $R^8$ and $R^9$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
$R^{14}$ is selected from the group consisting of H, alkyl, substituted alkyl, aryl, substituted aryl, heteroaryl, substituted heteroaryl, heterocyclyl, substituted heterocyclyl, cycloalkyl, and substituted cycloalkyl; or X and $R^{14}$ are taken together to form a fused heterocyclyl group, substituted fused heterocycly group, fused heteroaryl group, or substituted fused heteroaryl group.

In another embodiment, one of $Z^1$ or $Z^2$ is selected from the group consisting of a xanthene, an indole and a borapolyazaindacine.

In a more particular embodiment, $Z^1$ or $Z^2$ is:

wherein,
$R^2$, $R^4$ and $R^{10}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
$R^3$ is selected from the group consisting of alkoxy, substituted alkoxy, amino, substituted amino, hydrazinyl, substituted hydrazinyl, analyte substituted hydrazinyl, alkyl, substituted alkyl, acyl, acylamino, acyloxy, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or
$R^2$ and $R^3$, $R^3$ and $R^4$, or $R^2$, $R^3$ and $R^4$ are taken together to form a fused heterocyclyl group, a fused substituted heterocyclyl group, a fused aryl group, a fused substituted aryl group, a fused heteroaryl group or a fused substituted heteroaryl group;
$R^{15}$ is selected from the group consisting of =O and =$^{(+)}$N$R^{16}R^{17}$; and
$R^{16}$ is selected from the group consisting of H, alkyl, substituted alkyl, aryl, substituted aryl, cycloalkyl, substituted cycloalkyl, heterocyclyl, substituted heterocyclyl, heteroaryl, and substituted heteroaryl; and
$R^{17}$ is selected from the group consisting of alkyl, substituted alkyl, amino, and substituted amino.

In a more particular embodiment, $R^{15}$ is =O. In another embodiment, $R^{15}$ is =$^{(+)}$N$R^{16}R^{17}$. In another embodiment, $R^{16}$ and $R^{17}$ are methyl. In another embodiment, $R^2$, $R^4$ and $R^{10}$ are H. In another embodiment, $R^3$ is amino or substituted amino. In another embodiment, $R^3$ is hydroxy. In another embodiment, $R^3$ is —N(CH$_3$)$_2$.

In another embodiment, $R^2$, $R^3$ and $R^4$ are taken together to form a fused heterocyclyl group or substituted fused heterocyclyl group of the following structure:

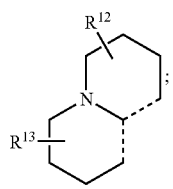

wherein, $R^{12}$ and $R^{13}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl.

In a more particular embodiment, $Z^1$ or $Z^2$ is:

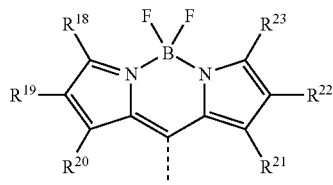

$R^{18}$, $R^{19}$, $R^{20}$, $R^{21}$, $R^{22}$, $R^{23}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, —$SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl.

In another embodiment, $R^{19}$ and $R^{22}$ are H. In another embodiment, $R^{18}$, $R^{20}$, $R^{21}$ and $R^{23}$ are methyl. In another embodiment, $R^{18}$, $R^{19}$, $R^{20}$, $R^{21}$, $R^{22}$ and $R^{23}$ are H.

In a more particular embodiment, $Z^1$ or $Z^2$ is:

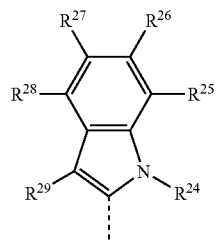

$R^{24}$ is selected from the group consisting of H, alkyl, substituted alkyl, aryl, substituted aryl, heteroaryl, substituted heteroaryl, cycloalkyl, substituted cycloalkyl, heterocyclyl, and substituted heterocyclyl; and $R^{25}$, $R^{26}$, $R^{27}$, $R^{28}$ and $R^{29}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, —$SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl.

In another embodiment thereof, $R^{24}$, $R^{25}$, $R^{27}$, $R^{28}$ and $R^{29}$ are H. In another embodiment, $R^{26}$ is a carboxyl ester. In another embodiment, $R^{26}$ is —$CO_2CH_3$. In another embodiment, $R^5$, $R^6$, $R^8$ and $R^{14}$ are all H. In another embodiment, $R^9$ is —$SO_3^-$. In another embodiment, $R^9$ is —$CO_2^-$.

In a more particular embodiment, X is H. In another embodiment, X is an analyte. More particularly still, the analyte is bound through an imine. In another embodiment, the analyte is selected from the group consisting of an amino acid, a peptide, a protein, a carbohydrate, a polysaccharide, a nucleoside, a nucleotide, an oligonucleotide, a nucleic acid polymer, a drug, a lipid, and a synthetic polymer. In another embodiment, the analyte comprises a carbonyl group. In another embodiment, the analyte comprises an aldehyde group. In another embodiment the analyte is malondialdehyde. In another embodiment the analyte is 4-hydroxynonenal.

In a more particular embodiment X and $R^{14}$ are taken together to form a fused heteroaryl or heterocyclyl group. More particular still, X and $R^{14}$ are taken together to form a pyrazole group.

Another aspect of the invention provides a compound of Formula VI:

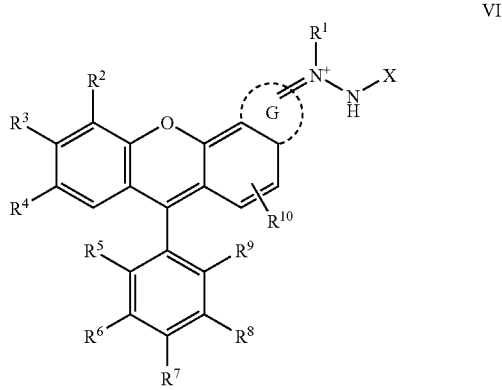

or a stereoisomer, tautomer, hydrate, solvate, or salt thereof;
wherein,
G is a 5-6 membered fused aryl or heteroaryl group;
X is H or an analyte;
$R^1$ is selected from the group consisting of H, alkyl and substituted alkyl;
$R^2$, $R^4$, $R^5$, $R^6$, $R^7$, $R^8$, $R^9$ and $R^{10}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^3$ is selected from the group consisting of alkoxy, substituted alkoxy, amino, substituted amino, hydrazinyl, substituted hydrazinyl, analyte substituted hydrazinyl, alkyl, substituted alkyl, acyl, acylamino, acyloxy, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or $R^2$ and $R^3$, $R^3$ and $R^4$, or $R^2$, $R^3$ and $R^4$ are taken together to form a fused heterocyclyl group, a fused substituted heterocyclyl group, a fused aryl group, a fused substituted aryl group, a fused heteroaryl group or a fused substituted heteroaryl group.

In another embodiment, G is a 6-membered aryl group. More particularly, G is phenyl. In a more particular embodiment thereof, the compound has the formula VI(a):

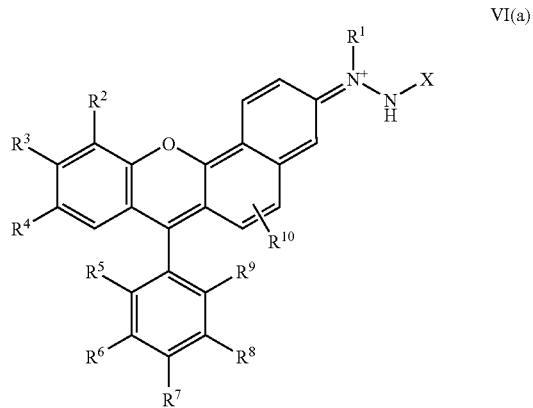

VI(a)

wherein each of the variables are described herein.

In another embodiment thereof, $R^1$ and $R^2$ are taken together to form a phenyl group.

In another embodiment, $R^1$ is H. Alternatively, $R^1$ is alkyl or substituted alkyl. In another embodiment, $R^3$ hydrazinyl or substituted hydrazinyl. In another embodiment, $R^3$ is methoxy. In another embodiment, $R^3$ is hydroxy. In another embodiment, $R^3$ is amino.

In another embodiment of the invention, $R^2$, $R^3$ and $R^4$ are taken together to form a fused heterocyclyl group or substituted fused heterocyclyl group of the formula:

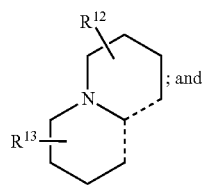

; and $R^{12}$ and $R^{13}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl.

In another embodiment, $R^4$, $R^5$, $R^6$, $R^7$, $R^8$ and $R^{10}$ are all H. In another embodiment, $R^2$, $R^4$, $R^5$, $R^6$, $R^7$, $R^8$ and $R^{10}$ are all H. In another embodiment, $R^9$ is —$SO_3^-$. In another embodiment, $R^9$ is —$CO_2^-$. In another embodiment, X is H. In another embodiment, $R^3$ is methoxy and $R^9$ is —$CO_2^-$.

In another embodiment of the invention, X is an analyte. In another embodiment, the analyte is bound through an imine. In another embodiment, the analyte is selected from the group consisting of an amino acid, a peptide, a protein, a carbohydrate, a polysaccharide, a nucleoside, a nucleotide, an oligonucleotide, a nucleic acid polymer, a drug, a lipid, and a synthetic polymer. In another embodiment, the analyte comprises a carbonyl group. In another embodiment, the analyte comprises an aldehyde group. In another embodiment, $R^3$ is analyte substituted hydrazinyl. In another embodiment, the analyte is bound through an imine. In another embodiment the analyte is malondialdehyde. In another embodiment the analyte is 4-hydroxynonenal.

Another aspect of the invention provides a composition comprising:
(a) an analyte; and
(b) a compound as described herein.

Another more particular aspect of the invention provides a composition comprising:
(a) an analyte; and
(b) a compound of Formula I:

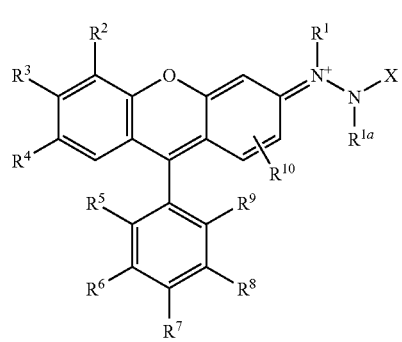

I or a stereoisomer, tautomer, hydrate, solvate, or salt thereof;
wherein,
X is H or an analyte;
$R^1$ and $R^{1a}$ are independently selected from the group consisting of H, alkyl and substituted alkyl;
$R^2$, $R^4$, $R^5$, $R^6$, $R^7$, $R^8$, $R^9$ and $R^{10}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^3$ is selected from the group consisting of alkoxy, substituted alkoxy, amino, substituted amino, hydrazinyl, alkyl, substituted alkyl, acyl, acylamino, acyloxy, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or $R^2$ and $R^3$, $R^3$ and $R^4$, or $R^2$, $R^3$ and $R^4$ are taken together to form a fused heterocyclyl group, a fused substituted heterocyclyl group, a fused aryl group, a fused substituted aryl group, a fused heteroaryl group or a fused substituted heteroaryl group.

A more particular embodiment further comprises a buffer solution. Another embodiment provides an additional dye in solution. The additional dye may be another aldehyde/ketone sensitive dye or not. Additional dyes are well known in the art and include those described in The Handbook, A guide to Fluorescent Probes and Labeling Technologies, by R. Haugland, 10th Edition.

In another embodiment of the composition, the analyte is selected from the group consisting of: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus.

A more particular aspect of the composition provides any of the above embodiments, particularly those describing $R^1$-$R^{10}$ and X.

Another aspect of the invention provides a method for determining the presence of an analyte of interest in a sample, wherein the method comprises:
  contacting the sample with a compound described herein;
  incubating the sample and the compound for a sufficient amount of time to form a complex between the compound and analyte;
  illuminating the complex with an appropriate wavelength to form an illuminated complex; and
  detecting emissions from the illuminated complex.

Another more particular aspect of the invention provides a method for determining the presence of an analyte of interest in a sample, wherein the method comprises:
  contacting the sample with a compound having Formula I:

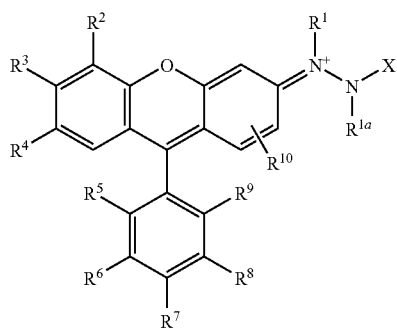

I or a stereoisomer, tautomer, hydrate, solvate, or salt thereof;

wherein,

X is H or an analyte;

$R^1$ and $R^{1a}$ are independently selected from the group consisting of H, alkyl and substituted alkyl;

$R^2$, $R^4$, $R^5$, $R^6$, $R^7$, $R^8$, $R^9$ and $R^{10}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^3$ is selected from the group consisting of alkoxy, substituted alkoxy, amino, substituted amino, hydrazinyl, alkyl, substituted alkyl, acyl, acylamino, acyloxy, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or $R^2$ and $R^3$, $R^3$ and $R^4$, or $R^2$, $R^3$ and $R^4$ are taken together to form a fused heterocyclyl group, a fused substituted heterocyclyl group, a fused aryl group, a fused substituted aryl group, a fused heteroaryl group or a fused substituted heteroaryl group;
  incubating the sample and the compound for a sufficient amount of time to form a complex between the compound and analyte;
  illuminating the complex with an appropriate wavelength to form an illuminated complex; and
  detecting emissions from the illuminated complex.

In another embodiment, the analyte and the compound are connected by a covalent bond. In another embodiment, the compound becomes fluorescent after formation of the complex. In another embodiment, the analyte is bound to the compound through an imine. In another embodiment, the analyte is selected from the group consisting of: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus. In another embodiment, the analyte comprises a carbonyl group. In another embodiment, the analyte comprises an aldehyde group. In another embodiment the analyte is malondialdehyde. In another embodiment the analyte is 4-hydroxynonenal.

In another embodiment, the sample comprises live cells, intracellular fluids, extracellular fluids, biological fluids, biological fermentation media, environmental sample, industrial samples, proteins, peptides, buffer solutions biological fluids or chemical reactors. In another embodiment, the sample comprises blood cells, immune cells, cultured cells, muscle tissue, neurons, extracellular vesicles; vascular tissue, blood fluids, saliva, urine; water, soil, waste water, sea water; pharmaceuticals, foodstuffs or beverages. In another embodiment, the sample is immobilized on a polymeric membrane, within a polymeric gel, on a microparticle, on a microarray, on a silicon chip, on a glass slide, on a microwell plate, and on a microfluidic chip.

Another aspect of the invention provides a kit for detecting an analyte in a sample, wherein the kit comprises:
a compound as describe herein that binds the analyte; and
instructions for detecting the analyte.

Another aspect of the invention provides a kit for detecting an analyte in a sample, wherein the kit comprises:
a compound of Formula I that binds the analyte:

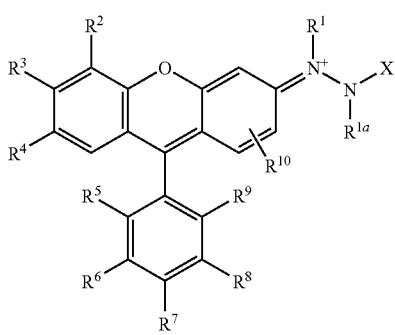

I or a stereoisomer, tautomer, hydrate, solvate, or salt thereof;
wherein,
X is H or an analyte;
$R^1$ and $R^{1a}$ are independently selected from the group consisting of H, alkyl and substituted alkyl;
$R^2$, $R^4$, $R^5$, $R^6$, $R^7$, $R^8$, $R^9$ and $R^{10}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;
$R^3$ is selected from the group consisting of alkoxy, substituted alkoxy, amino, substituted amino, hydrazinyl, alkyl, substituted alkyl, acyl, acylamino, acyloxy, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or
$R^2$ and $R^3$, $R^3$ and $R^4$, or $R^2$, $R^3$ and $R^4$ are taken together to form a fused heterocyclyl group, a fused substituted heterocyclyl group, a fused aryl group, a fused substituted aryl group, a fused heteroaryl group or a fused substituted heteroaryl group; and
instructions for detecting the analyte.

A more particular embodiment further comprises instructions for covalently bonding the compound to the analyte. A more particular embodiment further comprising one or more of the following: a buffering agent, a purification medium, a vial comprising the analyte, or an organic solvent.

Another aspect of the invention provides a compound comprising a (9-phenyl-3H-xanthen-3-ylidene)hydrazine, wherein the hydrazine group is unsubstituted or substituted with an analyte. In another more particular embodiment thereof, (9-phenyl-3H-xanthen-3-ylidene)hydrazine is substituted with methoxy, amino, sulfonyl, carboxyl, sulfonylalkyl, alkyl, or a second hydrazinyl group. More particular still, the (9-phenyl-3H-xanthen-3-ylidene)hydrazine is (E)-(9-phenyl-3H-xanthene-6-yl-3-ylidene)bis(hydrazine). In another embodiment, the analyte comprises an aldehyde group.

Another aspect of the invention provides a composition comprising:
(a) an analyte; and
(b) a compound of Formula V:

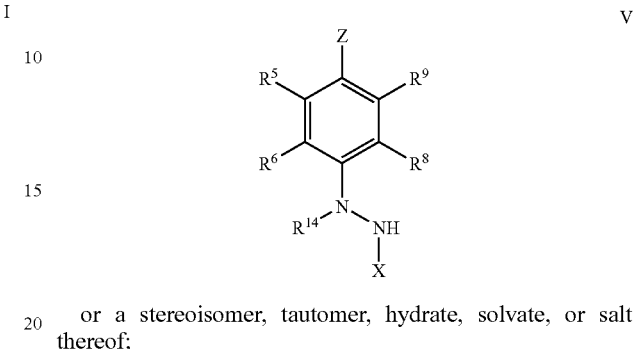

V or a stereoisomer, tautomer, hydrate, solvate, or salt thereof;
wherein,
X is H or an analyte;
Z is a fluorophore;
$R^5$, $R^6$, $R^8$ and $R^9$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
$R^{14}$ is selected from the group consisting of H, alkyl, substituted alkyl, aryl, substituted aryl, heteroaryl, substituted heteroaryl, heterocyclyl, substituted heterocyclyl, cycloalkyl, and substituted cycloalkyl; or
X and $R^{14}$ are taken together to form a fused heterocyclyl group, substituted fused heterocycly group, fused heteroaryl group, or substituted fused heteroaryl group.

Another more particular embodiment further comprises a buffer solution. In another embodiment, the analyte is selected from the group consisting of: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus.

Another aspect of the invention provides a method for determining the presence of an analyte of interest in a sample, wherein the method comprises:
contacting the sample with compound of Formula V:

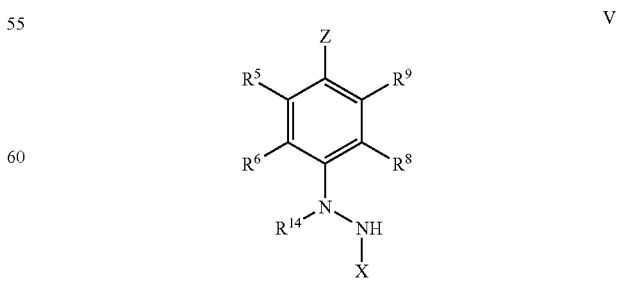

V or a stereoisomer, tautomer, hydrate, solvate, or salt thereof;

wherein,

X is H or an analyte;

Z is a fluorophore;

$R^5$, $R^6$, $R^8$ and $R^9$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^{14}$ is selected from the group consisting of H, alkyl, substituted alkyl, aryl, substituted aryl, heteroaryl, substituted heteroaryl, heterocyclyl, substituted heterocyclyl, cycloalkyl, and substituted cycloalkyl; or X and $R^{14}$ are taken together to form a fused heterocyclyl group, substituted fused heterocycly group, fused heteroaryl group, or substituted fused heteroaryl group;

incubating the sample and the compound for a sufficient amount of time to form a complex between the compound and analyte;

illuminating the complex with an appropriate wavelength to form an illuminated complex; and detecting emissions from the illuminated complex.

In another embodiment, the analyte and the compound are connected by a covalent bond. In another embodiment, the compound becomes fluorescent after formation of the complex. In another embodiment, the analyte is bound to the compound through an imine. In another embodiment, the analyte is selected from the group consisting of: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus. In another embodiment, the analyte comprises a carbonyl group. In another embodiment, the analyte comprises an aldehyde group. In another embodiment the analyte is malondialdehyde. In another embodiment the analyte is 4-hydroxynonenal.

In another embodiment, the sample comprises live cells, intracellular fluids, extracellular fluids, biological fluids, biological fermentation media, environmental sample, industrial samples, proteins, peptides, buffer solutions biological fluids or chemical reactors. In another embodiment, the sample comprises blood cells, immune cells, cultured cells, muscle tissue, neurons, extracellular vesicles; vascular tissue, blood fluids, saliva, urine; water, soil, waste water, sea water; pharmaceuticals, foodstuffs or beverages. In another embodiment, the sample is immobilized on a polymeric membrane, within a polymeric gel, on a microparticle, on a microarray, on a silicon chip, on a glass slide, on a microwell plate, and on a microfluidic chip.

Another aspect of the invention provides a kit for detecting an analyte in a sample, wherein the kit comprises:

a compound of Formula V that binds the analyte:

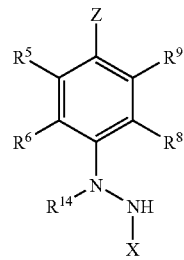

V or a stereoisomer, tautomer, hydrate, solvate, or salt thereof;

wherein,

X is H;

Z is a fluorophore;

$R^5$, $R^6$, $R^8$ and $R^9$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^{14}$ is selected from the group consisting of H, alkyl, substituted alkyl, aryl, substituted aryl, heteroaryl, substituted heteroaryl, heterocyclyl, substituted heterocyclyl, cycloalkyl, and substituted cycloalkyl; or X and $R^{14}$ are taken together to form a fused heterocyclyl group, substituted fused heterocycly group, fused heteroaryl group, or substituted fused heteroaryl group; and instructions for detecting the analyte.

Another embodiment thereof further comprises instructions for covalently bonding the compound to the analyte.

Another embodiment thereof further comprises one or more of the following: a buffering agent, a purification medium, a vial comprising the analyte, or an organic solvent.

Another aspect of the invention provides a method of synthesizing a compound of Formula III, a tautomer thereof, a stereoisomer thereof, or a salt thereof:

III or a stereoisomer, tautomer, hydrate, solvate, or salt thereof;

wherein, $R^1$ and $R^{11}$ are each independently selected from the group consisting of H, alkyl, substituted alkyl, aryl, substituted aryl, heteroaryl, substituted heteroaryl, heterocyclyl, substituted heterocyclyl, cycloalkyl, and substituted cycloalkyl;

$R^2$, $R^4$, $R^5$, $R^6$, $R^7$, $R^8$ and $R^{10}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

the method comprising:

contacting a compound of formula IV:

IV with $R^1$—NH—NH—$R^{12}$ and $R^{11}$—NH—NH—$R^{12}$, wherein $R^{12}$ is a protecting group, thereby obtaining a compound of Formula III(a):

III(a)

contacting $R^{12}$ with a deprotecting reagent, thereby obtaining a compound of Formula III.

In another embodiment the $SO_3^-$ group in formula III is a $CO_2^-$ and the $SO_2$ group is a CO.

In another embodiment, the protecting group is Boc. In another embodiment, the deprotecting reagent comprises an acid. In another embodiment, the acid is trifluoroacetic acid (TFA).

Another embodiment further comprises a purifying step after obtaining the compound of Formula III(a). Another embodiment further comprises a purifying step after obtaining the compound of Formula III. In another embodiment, the purifying step comprises at least one of: column chromatography, trituration, recrystallization, filtration, or aqueous separation.

Another embodiment further comprises synthesizing a compound of Formula IV, comprising:

(c) contacting a compound of Formula IV(a):

IV(a)

with a chlorinating agent, thereby obtaining the compound of Formula IV.

In another embodiment, the chlorinating agent comprises $PCl_5$ or $POCl_3$.

Another embodiment further comprises a purifying step after obtaining the compound of Formula IV. In another embodiment, the purifying step comprises at least one of: column chromatography, trituration, recrystallization, filtration, or aqueous separation.

One particular synthetic example is provided in Scheme 1:

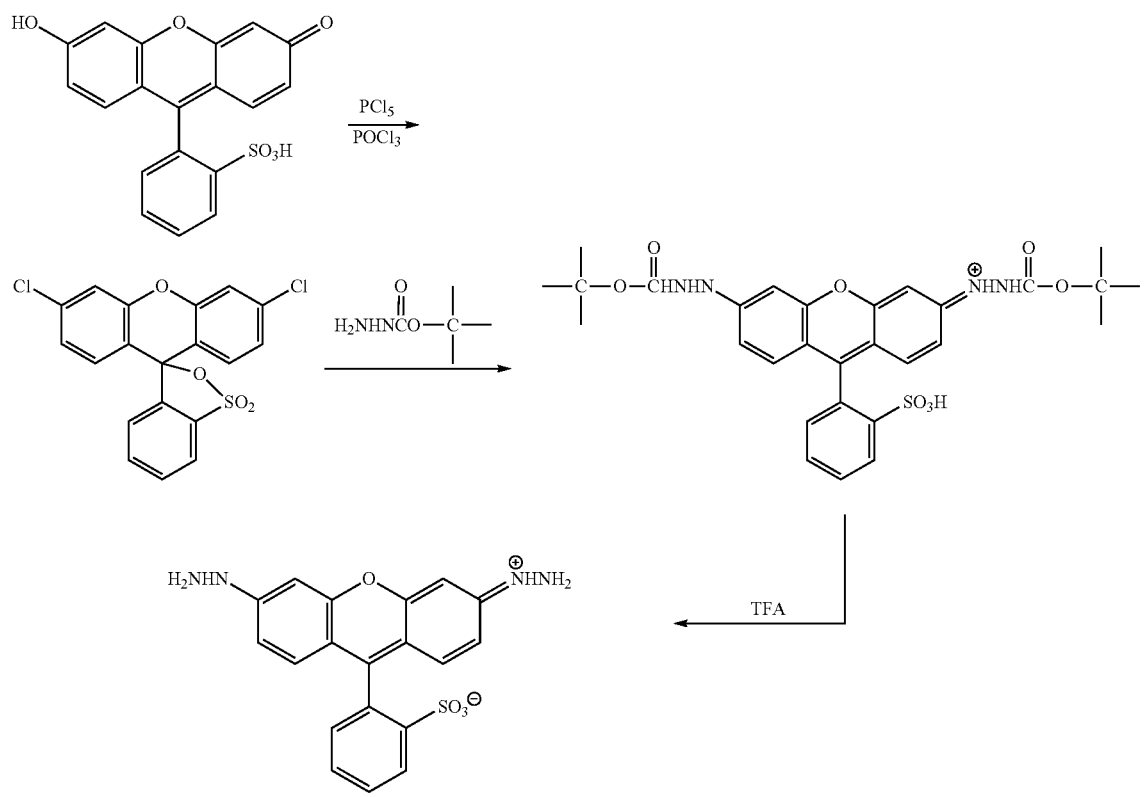

Various ancillary materials will frequently be employed in an assay in accordance with the present invention. In an exemplary embodiment, buffers and/or stabilizers are present in the kit components. In another exemplary embodiment, the kits comprise indicator solutions or indicator "dipsticks", blotters, culture media, cuvettes, and the like. In yet another exemplary embodiment, the kits comprise indicator cartridges (where a kit component is bound to a solid support) for use in an automated detector. In another exemplary embodiment, the kit further comprises molecular weight markers, wherein said markers are selected from phosphorylated and non-phosphorylated polypeptides, calcium-binding and non-calcium binding polypeptides, sulfonated and non-sulfonated polypeptides, and sialylated and non-sialylated polypeptides. In another exemplary embodiment, the kit further comprises a member selected from a fixing solution, a detection reagent, a standard, a wash solution, and combinations thereof.

In an exemplary embodiment, the compounds of the invention comprise a reactive group which is a member selected from an acrylamide, an activated ester of a carboxylic acid, an acyl azide, an acyl nitrile, an aldehyde, an alkyl halide, an anhydride, an aniline, an aryl halide, an azide, an aziridine, a boronate, a carboxylic acid, a diazoalkane, a haloacetamide, a halotriazine, a hydrazine, a hydrazide, an imido ester, an isocyanate, an isothiocyanate, a maleimide, a phosphoramidite, a reactive platinum complex, a sulfonyl halide, a thiol group, and a photoactivatable group.

These reactive groups can be covalently attached either during or after the synthesis of the dyes in order to provide reactive group-containing-dyes. In this way, reactive group-containing-dyes can be covalently attached to a wide variety of carrier molecules or solid supports that contain or are modified to contain functional groups with suitable reactivity, resulting in chemical attachment of the components. In an exemplary embodiment, the reactive group of a compound of the invention and the functional group of the carrier molecule of solid support comprise electrophiles and nucleophiles that can generate a covalent linkage between them. Alternatively, the reactive group comprises a photoactivatable group, which becomes chemically reactive only after illumination with light of an appropriate wavelength. Typically, the conjugation reaction between the reactive group and the carrier molecule/solid support results in one or more atoms of the reactive group being incorporated into a new linkage attaching the dye to the carrier molecule/solid support. Selected examples of functional groups and linkages are shown in Table 1, where the reaction of an electrophilic group and a nucleophilic group yields a covalent linkage.

TABLE 1

Examples of some routes to useful covalent linkages with electrophile and nucleophile reactive groups

| Electrophilic Group | Nucleophilic Group | Resulting Covalent Linkage |
|---|---|---|
| activated esters* | amines/anilines | Carboxamides |
| acyl azides** | amines/anilines | Carboxamides |
| acyl halides | amines/anilines | Carboxamides |
| acyl halides | alcohols/phenols | Esters |
| acyl nitriles | alcohols/phenols | Esters |
| acyl nitriles | amines/anilines | Carboxamides |
| Aldehydes | amines/anilines | Imines |
| aldehydes or ketones | hydrazines | Hydrazones |
| aldehydes or ketones | hydroxylamines | Oximes |
| alkyl halides | amines/anilines | alkyl amines |
| alkyl halides | Carboxylic acids | Esters |

TABLE 1-continued

Examples of some routes to useful covalent linkages
with electrophile and nucleophile reactive groups

| Electrophilic Group | Nucleophilic Group | Resulting Covalent Linkage |
|---|---|---|
| alkyl halides | Thiols | Thioethers |
| alkyl halides | alcohols/phenols | Ethers |
| alkyl sulfonates | Thiols | Thioethers |
| alkyl sulfonates | Carboxylic acids | Esters |
| alkyl sulfonates | alcohols/phenols | Ethers |
| Anhydrides | alcohols/phenols | Esters |
| Anhydrides | amines/anilines | Carboxamides |
| aryl halides | Thiols | Thiophenols |
| aryl halides | Amines | aryl amines |
| Aziridines | Thiols | Thioethers |
| Boronates | Glycols | boronate esters |
| carboxylic acids | amines/anilines | Carboxamides |
| carboxylic acids | Alcohols | Esters |
| carboxylic acids | hydrazines | Hydrazides |
| Carbodiimides | Carboxylic acids | N-acylureas or anhydrides |
| Diazoalkanes | Carboxylic acids | Esters |
| Epoxides | Thiols | Thioethers |
| haloacetamides | Thiols | Thioethers |
| Halotriazines | amines/anilines | Aminotriazines |
| Halotriazines | alcohols/phenols | triazinyl ethers |
| imido esters | amines/anilines | Amidines |
| Isocyanates | amines/anilines | Ureas |
| Isocyanates | alcohols/phenols | Urethanes |
| isothiocyanates | amines/anilines | Thioureas |
| Maleimides | Thiols | Thioethers |
| phosphoramidites | Alcohols | phosphite esters |
| silyl halides | Alcohols | silyl ethers |
| sulfonate esters | amines/anilines | alkyl amines |
| sulfonate esters | Thiols | Thioethers |
| sulfonate esters | Carboxylic acids | Esters |
| sulfonate esters | Alcohols | Ethers |
| sulfonyl halides | amines/anilines | Sulfonamides |
| sulfonyl halides | phenols/alcohols | sulfonate esters |

*Activated esters, as understood in the art, generally have the formula —COΩ, where Ω is a good leaving group (e.g. oxysuccinimidyl (—OC$_4$H$_4$O$_2$) oxysulfosuccinimidyl (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are C$_1$-C$_6$ alkyl, C$_1$-C$_6$ perfluoroalkyl or C$_1$-C$_6$ alkoxy; or cyclohexyl, 3-dimethylaminopropyl, or N-morpholinoehtyl).
**Acyl azides can also rearrange to isocyanates In one aspect, the compound comprises (in addition to the reactive hydrazine) at least one reactive group that selectively reacts with an amine group. This amine-reactive group is selected from the group consisting of succinimidyl ester, sulfonyl halide, tetrafluorophenyl ester and iosothiocyanates. Thus, in one aspect, the present compounds form a covalent bond with an amine-containing molecule in a sample. In another aspect, the compound comprises at least one reactive group that selectively reacts with a thiol group. This thiol-reactive group is selected from the group consisting of maleimide, haloalkyl and haloacetamide (including any reactive groups disclosed in U.S. Pat. Nos. 5,362,628; 5,352,803 and 5,573,904).

Choice of the reactive group used to attach the compound of the invention to the substance to be conjugated typically depends on the reactive or functional group on the substance to be conjugated and the type or length of covalent linkage desired. The types of functional groups typically present on the organic or inorganic substances (biomolecule or non-biomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins.

Typically, the reactive group will react with an amine, a thiol, an alcohol, an aldehyde, a ketone, or with silica. Preferably, reactive groups react with an amine or a thiol functional group, or with silica. In one embodiment, the reactive group is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. No. 5,714,327.

Where the reactive group is an activated ester of a carboxylic acid, such as a succinimidyl ester of a carboxylic acid, a sulfonyl halide, a tetrafluorophenyl ester or an isothiocyanates, the resulting compound is particularly useful for preparing conjugates of carrier molecules such as proteins, nucleotides, oligonucleotides, or haptens. Where the reactive group is a maleimide, haloalkyl or haloacetamide (including any reactive groups disclosed in U.S. Pat. Nos. 5,362,628; 5,352,803 and 5,573,904 (supra)) the resulting compound is particularly useful for conjugation to thiol-containing substances. Where the reactive group is a hydrazide, the resulting compound is particularly useful for conjugation to periodate-oxidized carbohydrates and glycoproteins, and in addition is an aldehyde-fixable polar tracer for cell microinjection. Where the reactive group is a silyl halide, the resulting compound is particularly useful for conjugation to silica surfaces, particularly where the silica surface is incorporated into a fiber optic probe subsequently used for remote ion detection or quantification.

In a particular aspect, the reactive group is a photoactivatable group such that the group is only converted to a reactive species after illumination with an appropriate wavelength. An appropriate wavelength is generally a UV wavelength that is less than 400 nm. This method provides for specific attachment to only the target molecules, either in solution or immobilized on a solid or semi-solid matrix. In this way, present dye compounds that comprise a photoactivatable reactive group associate with anionic proteins and can be covalently conjugated to the proteins. Photoactivatable reactive groups include, without limitation, benzophenones, aryl azides and diazirines.

Preferably, the reactive group is a photoactivatable group, succinimidyl ester of a carboxylic acid, a haloacetamide, haloalkyl, a hydrazine, an isothiocyanate, a maleimide group, an aliphatic amine, a silyl halide, a cadaverine or a psoralen. More preferably, the reactive group is a succinimidyl ester of a carboxylic acid, a maleimide, an iodoacetamide, or a silyl halide. In a particular embodiment the reactive group is a succinimidyl ester of a carboxylic acid, a sulfonyl halide, a tetrafluorophenyl ester, an iosothiocyanates or a maleimide.

The selection of a covalent linkage to attach the reporter molecule to the carrier molecule or solid support typically depends on the chemically reactive group on the component to be conjugated. The discussion regarding reactive groups in the section immediately preceding is relevant here as well. In addition to the hydrazinyl appendage, exemplary reactive groups typically present on the biological or non-biological components include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. A single type of reactive site may be available on the component (typical for polysaccharides), or a variety of sites may occur (e.g. amines, thiols, alcohols, phenols), as is typical for proteins. A carrier molecule or solid support may be conjugated to more than one reporter molecule, which may be the same or different, or to a substance that is additionally modified by a hapten. Although some selectivity can be obtained by careful control of the reaction conditions, selectivity of labeling is best obtained by selection of an appropriate reactive compound.

In another exemplary embodiment, the dye is covalently bound to a carrier molecule. If the compound has a reactive group, then the carrier molecule can alternatively be linked to the compound through the reactive group. The reactive group may contain both a reactive functional moiety and a linker, or only the reactive functional moiety.

A variety of carrier molecules are useful in the present invention. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, and polymers.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In another exemplary embodiment, at least one member selected from $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$ and $R^{29}$ comprise a carrier molecule. In another exemplary embodiment one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$ and $R^{29}$ comprises a carrier group bound through a substituted alkyl group or reactive group, such as an -alkyl-succinamidyl group.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In a preferred embodiment the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In another preferred embodiment, the carrier molecule is an antibody or fragment thereof, an antigen, an avidin or streptavidin, a biotin, a dextran, an antibody binding protein, a fluorescent protein, agarose, and a non-biological microparticle. Typically, the carrier molecule is an antibody, an antibody fragment, antibody-binding proteins, avidin, streptavidin, a toxin, a lectin, or a growth factor. Preferred haptens include biotin, digoxigenin and fluorophores.

Antibody binging proteins include, but are not limited to, protein A, protein G, soluble Fc receptor, protein L, lectins, anti-IgG, anti-IgA, anti-IgM, anti-IgD, anti-IgE or a fragment thereof.

In an exemplary embodiment, the enzymatic substrate is selected from an amino acid, peptide, sugar, alcohol, alkanoic acid, 4-guanidinobenzoic acid, nucleic acid, lipid, sulfate, phosphate, —$CH_2OCO$alkyl and combinations thereof. Thus, the enzyme substrates can be cleave by enzymes selected from the group consisting of peptidase, phosphatase, glycosidase, dealkylase, esterase, guanidinobenzotase, sulfatase, lipase, peroxidase, histone deacetylase, endoglycoceramidase, exonuclease, reductase and endonuclease.

In another exemplary embodiment, the carrier molecule is an amino acid (including those that are protected or are substituted by phosphates, carbohydrates, or $C_1$ to $C_{22}$ carboxylic acids), or a polymer of amino acids such as a peptide or protein. In a related embodiment, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, or a growth factor. Exemplary haptens include biotin, digoxigenin and fluorophores.

In another exemplary embodiment, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In another exemplary embodiment, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In another exemplary embodiment, the carrier molecule comprises a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). In a related embodiment, the polysaccharide carrier molecule includes dextran, agarose or FICOLL.

In another exemplary embodiment, the carrier molecule comprises a lipid (typically having 6-25 carbons), including glycolipids, phospholipids, and sphingolipids. Alternatively, the carrier molecule comprises a lipid vesicle, such as a liposome, or is a lipoprotein (see below). Some lipophilic substituents are useful for facilitating transport of the conjugated dye into cells or cellular organelles.

Alternatively, the carrier molecule is cells, cellular systems, cellular fragments, or subcellular particles. Examples of this type of conjugated material include virus particles, bacterial particles, virus components, biological cells (such as animal cells, plant cells, bacteria, or yeast), or cellular components. Examples of cellular components that can be labeled, or whose constituent molecules can be labeled, include but are not limited to lysosomes, endosomes, cytoplasm, nuclei, histones, mitochondria, Golgi apparatus, endoplasmic reticulum and vacuoles.

In another embodiment the carrier molecule is a metal chelating moiety. While any chelator that binds a metal ion of interest and gives a change in its fluorescence properties is a suitable conjugate, preferred metal chelating moieties are crown ethers, including diaryldiaza crown ethers, as described in U.S. Pat. No. 5,405,975 to Kuhn et al. (1995); derivatives of 1,2-bis-(2-aminophenoxyethane)-N,N,N',N'-tetraacetic acid (BAPTA), as described in U.S. Pat. No. 5,453,517 to Kuhn et al. (1995) (incorporated by reference) and U.S. Pat. No. 5,049,673 to Tsien et al. (1991); derivatives of 2-carboxymethoxy-aniline-N,N-diacetic acid (APTRA), as described by Ragu et al., Am. J. Physiol., 256: C540 (1989); and pyridyl-based and phenanthroline metal ion chelators, as described in U.S. Pat. No. 5,648,270 to Kuhn et al. (1997).

Aldehyde/ketone-sensing conjugates of the invention are optionally prepared in chemically reactive forms and further conjugated to polymers such as dextrans to improve their utility as sensors as described in U.S. Pat. Nos. 5,405,975 and 5,453,517.

In another exemplary embodiment, the carrier molecule non-covalently associates with organic or inorganic materials. Exemplary embodiments of the carrier molecule that possess a lipophilic substituent can be used to target lipid assemblies such as biological membranes or liposomes by non-covalent incorporation of the dye compound within the membrane, e.g., for use as probes for membrane structure or for incorporation in liposomes, lipoproteins, films, plastics, lipophilic microspheres or similar materials.

In an exemplary embodiment, the carrier molecule comprises a specific binding pair member wherein the present compounds are conjugated to a specific binding pair member and are used to detect an analyte in a sample. Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. Exemplary binding pairs are set forth in Table 2.

TABLE 2

Representative Specific Binding Pairs

| Antigen | Antibody |
|---|---|
| Biotin | avidin (or streptavidin or anti-biotin) |
| IgG* | protein A or protein G |
| Drug | drug receptor |
| Folate | folate binding protein |
| Toxin | toxin receptor |
| Carbohydrate | lectin or carbohydrate receptor |
| Peptide | peptide receptor |
| Protein | protein receptor |
| enzyme substrate | Enzyme |
| DNA (RNA) | cDNA (cRNA)† |
| Hormone | hormone receptor |
| Ion | Chelator |
| Antibody | antibody-binding proteins |

*IgG is an immunoglobulin
†cDNA and cRNA are the complementary strands used for hybridization Analytes:

Analytes of interest are preferably bound through a hydrazinyl group on the dye or a reporter moiety bound to the dye. The analytes include: an amino acid, a peptide, a protein, a carbohydrate, a polysaccharide, a nucleoside, a nucleotide, an oligonucleotide, a nucleic acid polymer, a hapten, a psoralen, a drug, a hormone, a lipid, a lipid assembly, a synthetic polymer, a biotin-binding protein, a polymeric microparticle, a biological cell and a virus. In another embodiment, the analyte comprises a carbonyl group. In another embodiment, the analyte comprises an aldehyde or ketone group. In another embodiment the analyte is malondialdehyde. In another embodiment the analyte is 4-hydroxynonenal.

In one embodiment the analyte described herein is a result of oxidative stress, such as from interaction with a superoxide, hydroxy, peroxy, alkoxy, hydroperoxy, hydrogenperoxide, hypochlorous acid, ozone, a singlet oxygen, or peroxynitrite. In another embodiment the analyte is indicative of activity or inactivity of superoxide dismutase, catalase, glutathione peroxidase or substrates relating thereto, including, vitamin A, E, ascorbate or glutathione. In another embodiment, the analyte is a biomarker for a disease such as alzheimers, parkinsons, atherosclerosis, multiple sclerosis, or cancer.

In a preferred embodiment the analyte is a result of a ROS (reactive oxygen species) pathway. In another embodiment the analyte is a product of lipid peroxidation. More particularly, the analyte is malonidialdehye.

In another embodiment, the sample comprises live cells, intracellular fluids, extracellular fluids, biological fluids, biological fermentation media, environmental sample, industrial samples, proteins, peptides, buffer solutions biological fluids or chemical reactors. In another embodiment, the sample comprises blood cells, immune cells, cultured cells, muscle tissue, neurons, extracellular vesicles; vascular tissue, blood fluids, saliva, urine; water, soil, waste water, sea water; pharmaceuticals, foodstuffs or beverages. In another embodiment, the sample is immobilized on a polymeric membrane, within a polymeric gel, on a microparticle, on a microarray, on a silicon chip, on a glass slide, on a microwell plate, and on a microfluidic chip.

Illumination

The sample or medium in which the aldehyde/ketone sensitive dye is present is illuminated with a wavelength of light selected to give a detectable optical response, and observed with a means for detecting the optical response. Equipment that is useful for illuminating the present compounds and compositions of the invention includes, but is not limited to, hand-held ultraviolet lamps, mercury arc lamps, xenon lamps, lasers and laser diodes. These illumination sources are optically integrated into laser scanners, fluorescence microplate readers or standard or microfluorometers.

The dyes of the invention may, at any time after or during an assay, be illuminated with a wavelength of light that results in a detectable optical response, and observed with a means for detecting the optical response. Upon illumination, such as by an ultraviolet or visible wavelength emission lamp, an arc lamp, a laser, or even sunlight or ordinary room light, the fluorescent compounds, including those bound to the complementary specific binding pair member, display intense visible absorption as well as fluorescence emission. Selected equipment that is useful for illuminating the fluorescent compounds of the invention includes, but is not limited to, hand-held ultraviolet lamps, mercury arc lamps, xenon lamps, argon lasers, laser diodes, and YAG lasers. These illumination sources are optionally integrated into laser scanners, fluorescence microplate readers, standard or mini fluorometers, or chromatographic detectors. This fluorescence emission is optionally detected by visual inspection, or by use of any of the following devices: CCD cameras, video cameras, photographic film, laser scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, a fluorescence microscope or a fluorometer, the instrument is optionally used to distinguish and discriminate between the fluorescent compounds of the invention and a second fluorophore with detectably different optical properties, typically by distinguishing the fluorescence response of the fluorescent compounds of the invention from that of the second fluorophore. Where a sample is examined using a flow cytometer, examination of the sample optionally includes isolation of particles within the sample based on the fluorescence response by using a sorting device. In another embodiment, the illumination source is used to form a covalent bond between the present dye and an analyte of interest. In this instance the dye comprises a photoactivatable reactive group, such as those discussed above.

A detailed description of the invention having been provided above, the following examples are given for the purpose of illustrating the invention and shall not be construed as being a limitation on the scope of the invention or claims.

EXAMPLES

Example 1

Compound 1

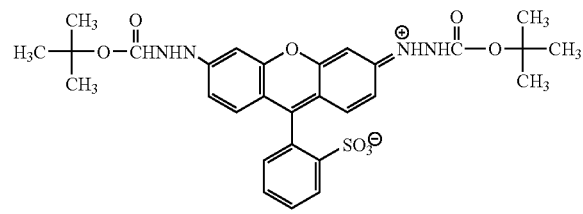

A mixture of 3,6-dichlorosulfofluoran (800 mg, 1.97 mmol) and tert-butyl carbazate (1.56 g, 11.82 mmol) in 15 ml of dry acetonitrile was stirred at 65° C. for 3 hours. The reaction mixture was then cooled to room temperature and the resulting orange-red solid collected by filtration to give 850 mg of Compound 1.

Example 2

Compound 2

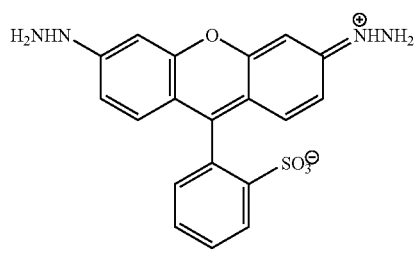

To an ice-cooled solution of 2 ml of trifluoroacetic acid was added Compound 1 (200 mg, 0.335 mmol) in a small portion over a 5-minute period. After stirring the ice-cooled temperature for 30 minutes, chloroform (about 10 ml) was added to the reaction mixture. The resulting orange-red solid was collected by filtration, washed with ether and dried under vacuum to give 160 mg of Compound 2.

Example 3

Compound 3

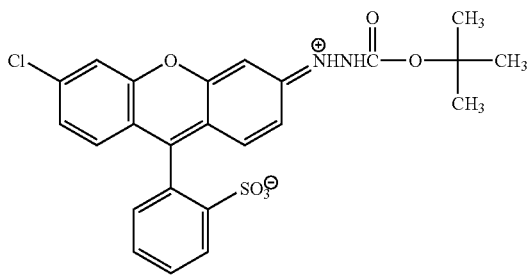

A mixture of 3,6-dichlorosulfofluoran (500 mg, 1.23 mmol) and tert-butyl carbazate (650 mg, 4.93 mmol) in 10 ml of dry acetonitrile was stirred at room temperature for 12 hours. After the reaction mixture was concentrated in vacuo, the resulting crude mixture was purified by column chromatography on silica gel eluting with 5/95 V/V methanol-chloroform to give 350 mg of Compound 3 orange solid.

Example 4

Compound 4

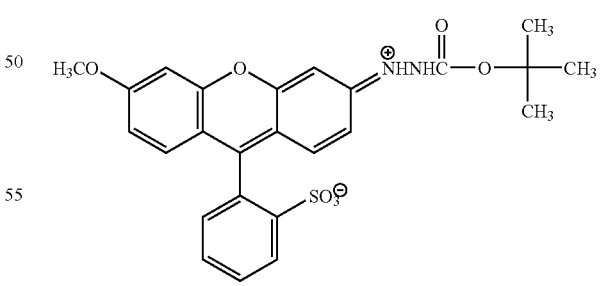

To a solution of Compound 3 (200 mg, 0.40 mmol) in 5 ml of dry N,N-dimethylformamide was added 1 ml of sodium methoxide solution in methanol (0.5 M) and the mixture was stirred at approximately 65° C. under nitrogen atmosphere for 5 hours. The resulting reaction mixture was cooled to room temperature and concentrated in vacuo. The crude product was then purified by column chromatography on silica gel eluting with 7% methanol in chloroform to give 125 mg of Compound 4 as orange solid.

Example 5

Compound 5

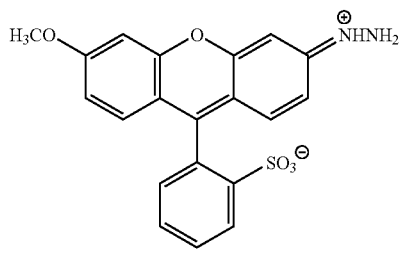

To an ice-cold solution of 1 ml of trifluoroacetic acid was added Compound 4 (150 mg, 0.30 mmol) in a small portion over a 5-minute period. After stirring for 30 minutes, the resulting solid was collected by filtration, washed with ether and dried in vacuo to give 72 mg of Compound 5 as orange solid.

Example 6

Compound 6

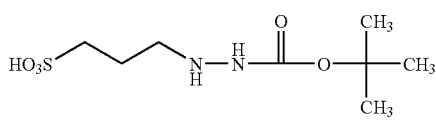 [SMILES: CC(C)(C)OC(=O)NNCCCS(=O)(=O)O]

To a solution of tert-butyl carbazate (2 g, 15 mmol) in 10 ml acetonitrile was added 1,3-propanesulfone (0.67 ml, 7.5 mmol) and the mixture was stirred at room temperature for two days. All the solvent was then removed in vacuo and the resulting crude product was purified by column chromatography on silica gel eluting with 25% methanol in chloroform to give 1.8 g of Compound 6 as off-white solid.

Example 7

Compound 7

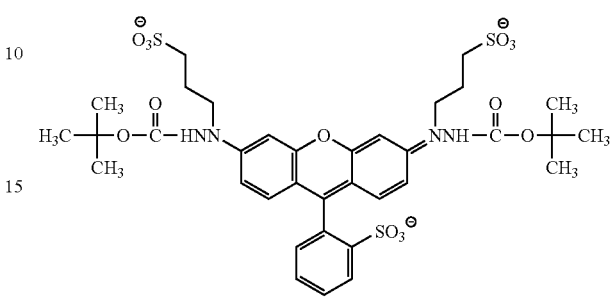

A sample of 3,6-dichlorofluoran (100 mg, 0.25 mmol) and Compound 6 (156 mg, 0.62 mmol) were dissolved in a mixture of 10 ml of acetonitrile and 4 ml of N,N-dimethylforamide. After stirring at 65° C. for 2 hours, all the solvent was removed in vacuo and the resulting crude material was purified by column chromatography over LH-20 Sephadex eluting with water to give 80 mg of Compound 7 as orange-red solid.

Example 8

Compound 8

To an ice-cold solution of 1 ml of trifluoroacetic acid was added Compound 7 (50 mg, 0.06 mmol) in a small portion over a 5-minute period. After stirring at ice-cold temperature for one hour, chloroform (about 10 ml) was added to the reaction mixture. The resulting orange-red solid was collected by filtration, washed with ether and dried under vacuum to give 26 mg of Compound 8 as orange-red solid.

Example 9

Compound 9

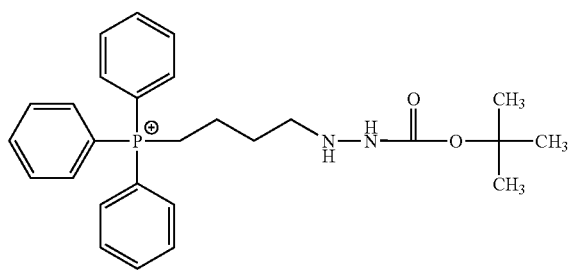 [SMILES: CC(C)(C)OC(=O)NNCCCC[P+](c1ccccc1)(c1ccccc1)c1ccccc1]

To a solution of tert-butylcarbazate (250 mg, 1.9 mmol) in 10 ml of acetonitrile was added a suspension of 4-bromobutyltriphenylphosphonium bromide (95 mg, 0.63 mmol) and the mixture was heated under reflux for 12 hours. All the solvent was removed in vacuo and the resulting crude product was purified by column chromatography over silica gel to give 250 mg of Compound 9 an off-white solid.

Example 10

Compound 10

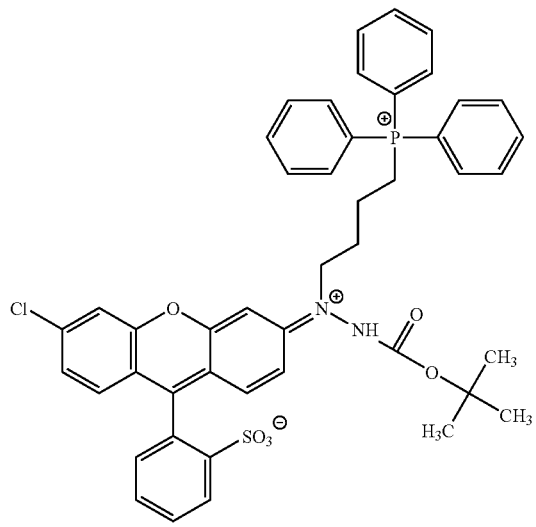

To a solution of 3,6-dichlorosulfofluoran (68 mg, 0.17 mmol) in 1 ml of N,N-dimethylformamide was added Compound 9 (90 mg, 0.17 mmol). After stirring at room temperature for 30 minutes, the mixture was concentrated in vacuo and the resulting crude product was purified by column chromatography over silica gel eluting with 20% methanol in chloroform to give 120 mg of Compound 10 as orange solid.

Example 11

Compound 11

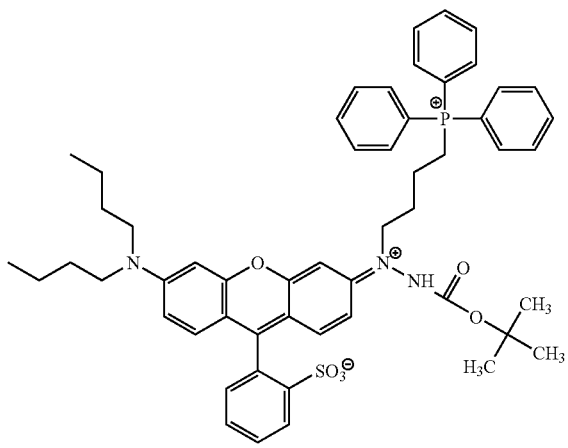

To a solution of Compound 10 (110 mg, 0.14 mmol) in 3 ml of dichloromethane was added dibutylamine (30 ul, 2 mmol) and the mixture was stirred near 60° C. for 12 hours. After removing all the solvent under vacuum, the resulting crude product was purified by column chromatography over silica gel eluting with 10% methanol in chloroform to give 68 mg of Compound 11 as orange-red solid.

Example 12

Compound 12

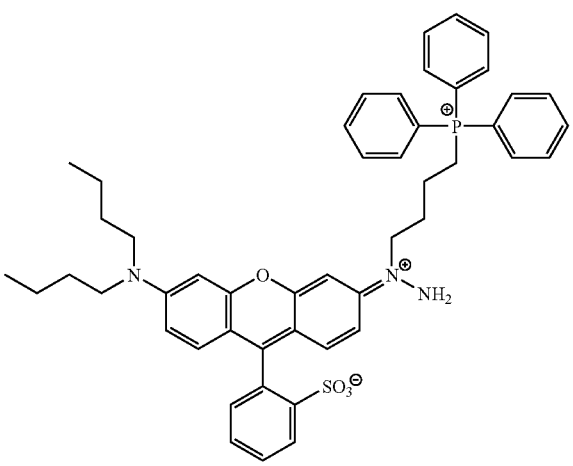

To an ice-cold solution of Compound 11 (20 mg, 0.02 mmol) in 1 ml of chloroform was added 250 ul of trifluoroacetic acid and the mixture was stirred at room temperature for 2 hours. All the solvent was removed under vacuum and the crude product was purified by column chromatography over silica gel eluting with water/methanol/chloroform (2:30:68 v/v/v) to give 10 mg of Compound 12 as red solid.

Compound Table

| Compound No. | Structure |
|---|---|
| 2 | (xanthene core with O bridge; 3-position: NH-NH$_2$ (hydrazinyl); 6-position: =N$^+$H-NH$_2$; 9-position: 2-sulfonatophenyl) |
| 5 | (xanthene core with O bridge; 3-position: OCH$_3$; 6-position: =N$^+$H-NH$_2$; 9-position: 2-sulfonatophenyl) |
| 8 | (xanthene core with O bridge; 3-position: N(CH$_2$CH$_2$CH$_2$SO$_3^-$)-NH$_2$; 6-position: =N$^+$(CH$_2$CH$_2$CH$_2$SO$_3^-$)-NH$_2$; 9-position: 2-sulfonatophenyl) |
| 13 | (xanthene core with O bridge; 3-position: NH$_2$; 6-position: =N$^+$H-NH$_2$; 9-position: 2-sulfonatophenyl) |
| 14 | (xanthene core with O bridge; 3-position: OCH$_3$; 6-position: =N$^+$(CH$_3$)-NH$_2$; 9-position: 2-carboxylatophenyl) |

-continued
| Compound No. | Structure |
|---|---|
| 15 | 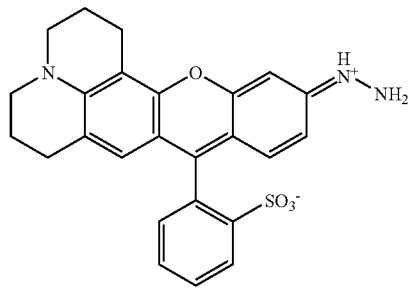 |
| 16 | 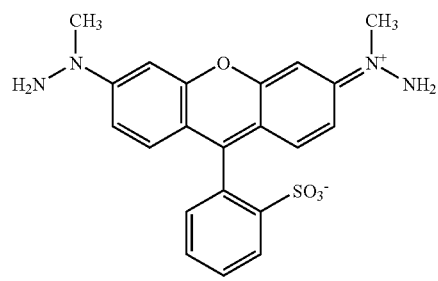 |
| 17 | 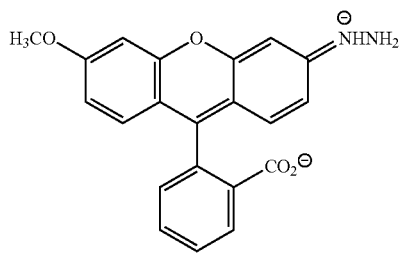 |
| 18 | 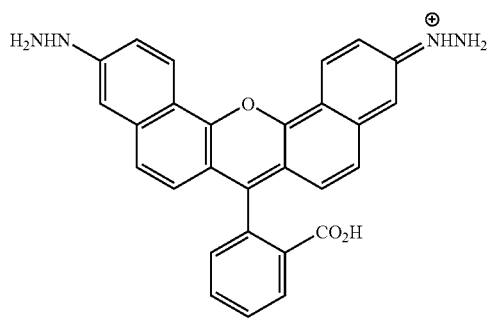 |
| 19 | 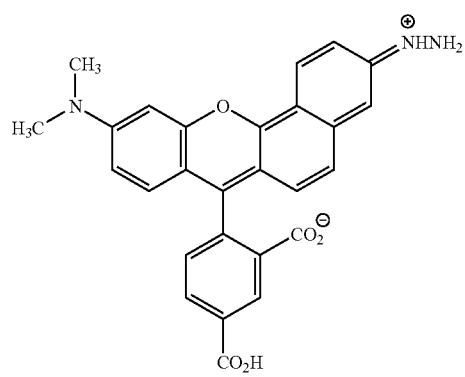 |

| Compound No. | Structure |
|---|---|
| 20 | *(structure: rhodamine-type xanthene with (H₃C)₂N– and –N⁺(CH₃)₂ groups, CO₂H, and HN–NH₂ substituent)* |
| 21 | *(structure: xanthene with HO– and =N⁺H–NH₂ groups, phenyl with SO₃⁻)* |
| 22 | *(BODIPY structure: BF₂-dipyrromethene with phenyl-HN-NH₂ substituent)* |

Example 13

Aldehyde Reactivity of Compounds

Figure 3A:
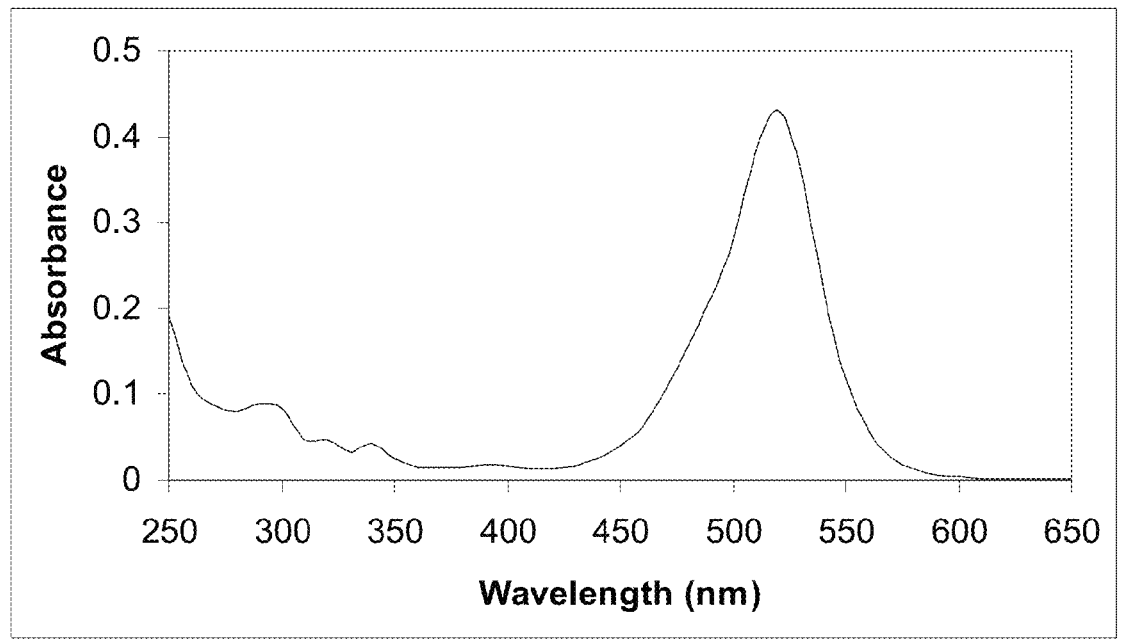
FIG. 3A shows the excitation maximum at 519 nm for un-reacted 2-(6-hydrazinyl-3-hydrazono-3H-xanthen-9-yl)benzenesulfonate. There were no fluorescent emissions detected from excitation at 519 nm.
Figure 3B:
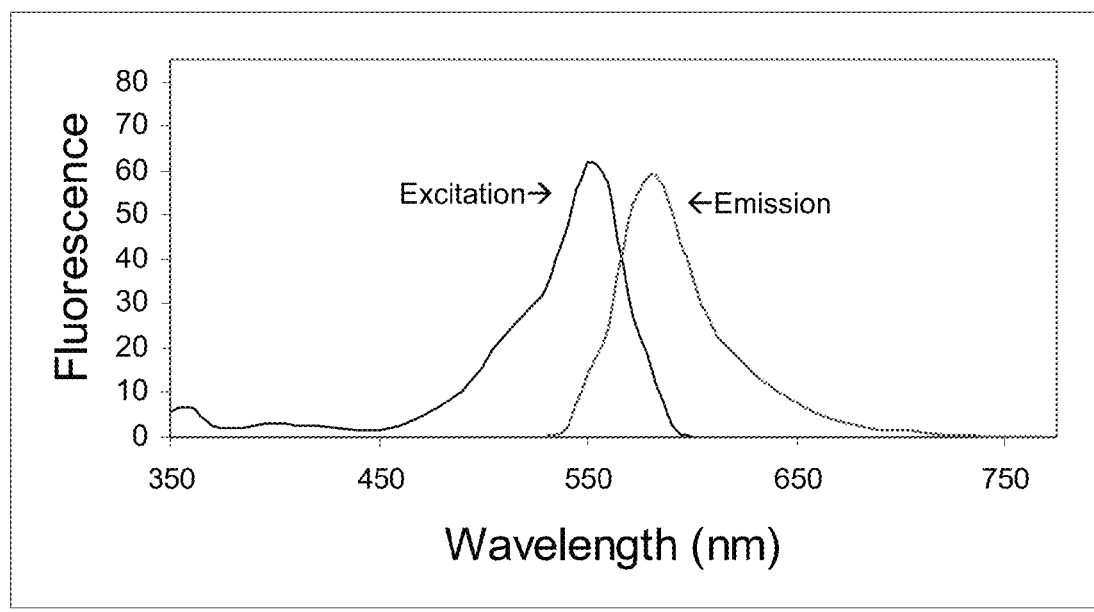
FIG. 3B shows excitation maximum at 548 nm for aldehyde-reacted 2-(6-hydrazinyl-3-hydrazono-3H-xanthen-9-yl)benzenesulfonate and a bright emmision spectra at 581 nm for the same species. Spectra were taken at pH 6 in 50 mM phosphate buffer solution.

A sample of Compound 2 (5 mg, 0.0126 mmol) is dissolved in 10 ml of pH 6.5, 50 mmol phosphate buffer solution. To this non-fluorescent solution, is added 25 ul, 1 mol solution of acetaldehyde in water at room temperature. Within a few minutes, the solution becomes highly fluorescent. The reaction is complete in 10 minutes to give a stable oxime analog. Its absorption max is at 548 nm and emission max is at 580 nm (see FIGS. 3A and B).

Each of the above-cited references are hereby incorporated by reference as if set forth fully herein.

The invention claimed is:

1. A kit for detecting an analyte in a sample, wherein the analyte contains an aldehyde group or a ketone group, wherein the kit comprises:

a compound of Formula I that binds the analyte:

*(Structure of Formula I: xanthene core with substituents $R^1$, $R^{1a}$, $R^2$, $R^3$, $R^4$, $R^5$, $R^6$, $R^7$, $R^8$, $R^9$, $R^{10}$, and X; with N⁺–N–X hydrazine moiety)*

I or a stereoisomer, tautomer, hydrate, solvate, or salt thereof;

wherein,

X is H;

$R^1$ is selected from the group consisting of H, alkyl and substituted alkyl;

$R^2$, $R^4$, $R^5$, $R^6$, $R^7$, $R^8$, $R^9$ and $R^{10}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^3$ is selected from the group consisting of alkoxy, substituted alkoxy, amino, substituted amino, hydrazinyl, alkyl, substituted alkyl, acyl, acylamino, acyloxy, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or $R^2$ and $R^3$, $R^3$ and $R^4$, or $R^2$, $R^3$ and $R^4$ are taken together to form a fused heterocyclyl group, a fused substituted heterocyclyl group, a fused aryl group, a fused substituted aryl group, a fused heteroaryl group or a fused substituted heteroaryl group; and instructions for detecting the analyte comprising the steps of:
contacting the sample with the compound;
incubating the sample and the compound for a sufficient amount of time to form a complex between the compound and analyte;
illuminating the complex with an appropriate wavelength to form an illuminated complex; and
detecting emissions from the illuminated complex;
wherein the hydrate or solvate thereof is a hydrate or solvate of an aqueous solution, an aqueous miscible solution, or a water-miscible organic solvent.

2. The kit of claim 1, further comprising instructions for covalently bonding the compound to the analyte.

3. The kit of claim 1, further comprising one or more of the following: a buffering agent, a purification medium, a vial comprising the analyte, or an organic solvent.

4. The kit of claim 1, wherein the analyte is malondialdehyde or 4-hydroxynonenal.

5. The kit of claim 1, wherein the analyte comprises an aldehyde group.

6. The kit of claim 1, wherein the sample comprises live cells, intracellular fluids, extracellular fluids, biological fluids, biological fermentation media, environmental sample, industrial samples, proteins, peptides, buffer solutions, or biological fluids.

7. The kit of claim 1, wherein the sample comprises blood cells, immune cells, cultured cells, muscle tissue, neurons, extracellular vesicles, vascular tissue, blood fluids, saliva, urine, water, soil, waste water, sea water, pharmaceuticals, foodstuffs or beverages.

8. The kit of claim 1, wherein the sample is immobilized on a polymeric membrane, within a polymeric gel, on a microparticle, on a microarray, on a silicon chip, on a glass slide, on a microwell plate, or on a microfluidic chip.

* * * * *

UNITED STATES PATENT AND TRADEMARK OFFICE
CERTIFICATE OF CORRECTION

PATENT NO. : 8,772,487 B2  
APPLICATION NO. : 12/864038  
DATED : July 8, 2014  
INVENTOR(S) : Aimei Chen et al.

Page 1 of 1

It is certified that error appears in the above-identified patent and that said Letters Patent is hereby corrected as shown below:

Column 66, lines 50-65, in Claim 1, please replace

"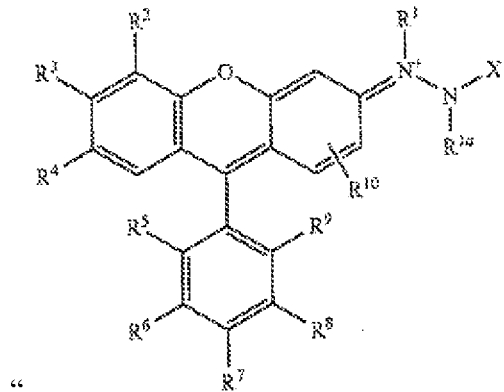" with "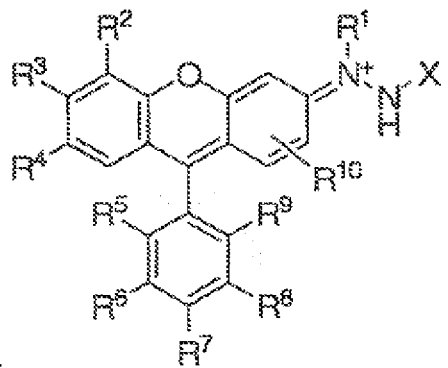"

--  --

Signed and Sealed this  
Ninth Day of August, 2016

Michelle K. Lee  
*Director of the United States Patent and Trademark Office*